US010413221B2

(12) United States Patent
Xing et al.

(10) Patent No.: US 10,413,221 B2
(45) Date of Patent: Sep. 17, 2019

(54) COMPOSITE MEMBRANE, BIOSENSOR, AND PREPARATION METHODS THEREOF

(71) Applicant: Shenzhen Kingsino Technology CO., LTD., Shenzhen (CN)

(72) Inventors: Malcolm Xing, Guangdong (CN); Haitao Shang, Guangdong (CN); Hong Wei, Guangdong (CN); Kun Jiang, Guangdong (CN)

(73) Assignee: SHENZHEN KINGSINO TECHNOLOGY CO., LTD., Shenzhen (CN)

( * ) Notice: Subject to any disclaimer, the term of this patent is extended or adjusted under 35 U.S.C. 154(b) by 414 days.

(21) Appl. No.: 15/337,900

(22) Filed: Oct. 28, 2016

(65) Prior Publication Data
US 2018/0116557 A1    May 3, 2018

(51) Int. Cl.
*B29D 99/00* (2010.01)
*A61B 5/113* (2006.01)
(Continued)

(52) U.S. Cl.
CPC ............ *A61B 5/113* (2013.01); *B29C 53/005* (2013.01); *B29C 55/005* (2013.01); *B29C 69/00* (2013.01);
(Continued)

(58) Field of Classification Search
CPC .......... A51B 2562/12; A51B 2562/125; A51B 2562/0261; B29C 53/005; B29C 53/02;
(Continued)

(56) References Cited

U.S. PATENT DOCUMENTS

| 7,988,896 B2 * | 8/2011 | Zhang | B29C 70/10 |
| | | | 264/128 |
| 2009/0032777 A1* | 2/2009 | Kitano | B82Y 30/00 |
| | | | 252/510 |

(Continued)

FOREIGN PATENT DOCUMENTS

WO    WO-2016182018 A1 *    11/2016    ............. B82Y 40/00

OTHER PUBLICATIONS

Darabi, Mohammad Ali et al. Gum Sensor: A Stretchable, Wearable, and Foldable Sensor Based on Carbon Nanotube/Chewing Gum Membrane, (ACS) Applied Materials & Interfaces, American Chemical Society. Nov. 2, 2015, vol. 7, pp. 26195-26205.

(Continued)

*Primary Examiner* — Eun Hwa Kim
*Assistant Examiner* — Catherine Premraj
(74) *Attorney, Agent, or Firm* — Hamre, Schumann, Mueller & Larson, P.C.

(57) ABSTRACT

A composite membrane, a biosensor, and preparation methods thereof are disclosed. In the preparation process, a moldable and plastic material is used as a carrier; after a dispersion liquid of a nanocarbon material wets the carrier, by means of multiple stretching and folding processes, the nanocarbon material is uniformly distributed and arranged regularly inside the entire plastic material in a stretching strain direction. The prepared composite membrane is elastic, attachable, and cost-efficient, and may detect strains as high as 530%. The composite membrane further has high sensitivity and high durability, and may be effectively applied to a biosensor for monitoring motion and humidity.

9 Claims, 15 Drawing Sheets

(51) Int. Cl.

| | |
|---|---|
| B29C 69/00 | (2006.01) |
| B29C 53/00 | (2006.01) |
| B29C 55/00 | (2006.01) |
| G01B 7/16 | (2006.01) |
| B29C 53/04 | (2006.01) |
| B29C 55/04 | (2006.01) |
| B29K 83/00 | (2006.01) |
| B29L 31/00 | (2006.01) |
| B29K 105/16 | (2006.01) |
| B29K 507/04 | (2006.01) |

(52) U.S. Cl.
CPC ............. *B29D 99/005* (2013.01); *G01B 7/18* (2013.01); *A61B 2562/0261* (2013.01); *A61B 2562/125* (2013.01); *B29C 53/04* (2013.01); *B29C 55/04* (2013.01); *B29K 2083/00* (2013.01); *B29K 2105/162* (2013.01); *B29K 2507/04* (2013.01); *B29K 2995/0005* (2013.01); *B29L 2031/753* (2013.01); *B29L 2031/755* (2013.01)

(58) Field of Classification Search
CPC ....... B29C 53/04; B29C 69/00; B29D 99/005; B29K 2083/00; B29K 2105/162; B29K 2507/04; B29K 2995/0005; B29L 2031/753; B29L 2031/755
See application file for complete search history.

(56) References Cited

U.S. PATENT DOCUMENTS

| | | | | |
|---|---|---|---|---|
| 2010/0154556 | A1* | 6/2010 | Yin | G01B 7/18 73/779 |
| 2011/0278040 | A1* | 11/2011 | Zhang | B29C 70/086 174/69 |
| 2012/0266685 | A1* | 10/2012 | Choi | G01L 1/20 73/774 |
| 2013/0118267 | A1* | 5/2013 | Suzuki | G01B 7/18 73/774 |
| 2016/0051939 | A1* | 2/2016 | Choi | B01D 69/122 210/500.3 |

OTHER PUBLICATIONS

Shen Fang-chao et al. Efficient Dispersion of Single-walled Carbon Nanotubes by Block Copolymer F127, Fine Chemicals. Dec. 2015, vol. 32, No. 12. 5 pages. Abstract in English.

Xia Kai-Lun et al., Advances in Wearable and Flexible Conductors Based on Nanocarbon Materials, Acta Physico-Chimica Sinica. Jul. 2016, vol. 32 No. 10, pp. 2427-2446. Abstract in English.

Yao, Wu et al. Research Status of the Dispersion of Carbon Nanotubes, China Academic Journal Electronic Publishing House. May 27, 2013. 6 pages. Abstract in English.

Son, Donghee et al. Multifunctional wearable devices for diagnosis and therapy of movement disorders, Nature Nanotechnology, Advance Online Publication. Mar. 30, 2014. <www.nature.com/naturenanotechnolgy>. 8 pages.

Gong, Shu et al., A wearable and highly sensitive pressure sensor with ultrathin gold nanowires, Nature Communications. Feb. 4, 2014, DOI: 10.1038/ncomms4132, <www.nature.com/naturecommunications>, 8 pages.

Pantelopoulos, Alexandros et al., A Survey on Wearable Sensor-Based Systems for Health Monitoring and Prognosis, IEEE Transactions on Systems, Man, and Cybernetics—Part C: Applications and Reviews, Jan. 2010, vol. 40, No. 1, 12 pages.

Gatzoulis, Loukianos et al., Wearable and Portable eHealth Systems, IEEE Engineering in Medicine and Biology Magazine. Sep./Oct. 2007, pp. 51-56.

Boland, Conor et al. Sensitive, High-Strain, High-Rate Bodily Motion Sensors Based on Graphene-Rubber Composites, American Chemical Society. Accepted Aug. 6, 2014. vol. XXX, No. XX, <www.acsnano.org>, pp. A-L.

Yamada, Takeo et al., A stretchable carbon nanotube strain sensor for human-motion detection, Nature Nanotechnology, Articles Published Online: Mar. 27, 2011. DOI: 10.1038/NNAN0.2011.36. May 2011, vol. 6, <www.nature.com/naturenanotechnolgy>, pp. 296-301.

Lipomi, Darren et al., Skin-like pressure and strain sensors based on transparent elastic films of carbon nanotubes, Nature Nanotechnology, Letters Published Online: Oct. 23, 2011. DOI: 10.1038/NNAN0.2011.184. vol. 6, Dec. 2011,<www.nature.com/naturenanotechnolgy>, pp. 788-792.

Pang, Changhyun et al., A flexible and highly sensitive strain-gauge sensor using reversible interlocking of nanofibres, Nature Materials, Articles Published Online: Jul. 29 , 2012. DOI: 10.1038/NMAT3380, <www.nature.com/naturematerials>, 7 pages.

Park, Minwoo et al., Highly stretchable electric circuits from a composite material of silver nanoparticles and elastomeric fibres, Nature Nanotechnology, Letters Published Online: Nov. 25, 2012. DOI: 10.1038/NNAN0.2012.206. vol. 7, Dec. 2012,<www.nature.com/naturenanotechnolgy>, pp. 803-809.

Lee, Jaehwan et al. A stretchable strain sensor based on a metal nanoparticle thin film for human motion detection, The Royal Society of Chemistry. Nanoscale, 2014, vol. 6, pp. 11932-11939.

Zeng, Wei et al. Fiber-Based Wearable Electronics: A Review of Materials, Fabrication, Devices, and Applications, Advanced Materials. 2014, Material Views. DOI: 10.1002/adma.201400633, 27 pages.

Axisa, Fabrice et al. Flexible Technologies and Smart Clothing for Citizen Medicine, Home Healthcare, and Disease Prevention, IEEE Transactions on Information Technology in Biomedicine, Sep. 2005, vol. 3, No. 3, pp. 325-336.

Mattmann, Corinne et al. Sensor for Measuring Strain in Textile, Sensors 2008, 8, DOI: 10.3390/s8063719. Published Jun. 3, 2008, pp. 3719-3732.

Zahab, A. et al. Water-vapor effect on the electrical conductivity of a single-walled carbon nanotube mat, The American Physical Society. Oct. 15, 2000, vol. 62, No. 15, Physical Review B, 4 pages.

Pati, Ranjit et al., Effect of H2O adsorption on electron transport in a carbon nanotube, Applied Physics Letters. Sep. 30, 2002, vol. 81, No. 14, 4 pages.

Varghese, O.K. et al. Gas sensing characteristics of multi-wall carbon nanotubes, Sensors and Actuators B. 2001, vol. 81, pp. 32-41.

Cao, C. L. et al. Humidity Sensor Based onMulti-Walled Carbon Nanotube Thin Films, Hindawi Publishing Corporation Journal of Nanomaterials, 2011, vol. 2011, Article ID 707303, 5 pages.

Fei, Teng et al. Humidity Switching Properties of Sensors Based on Multiwalled Carbon Nanotubes/Polyvinyl Alcohol Composite Films, Journal of Applied Polymer Science. 2013 Wiley Periodicals, Inc. No. 39726, 7 pages.

Yoo, Kum-Pyo et al. Novel resistive-type humidity sensor based on multiwall carbon nanotube/polyimide composite films, Sensors and Actuators B: Chemical. 2010, vol. 145, pp. 120-125.

Tang, Qing-Yuan et al. Fast response resistive humidity sensitivity of polyimide/multiwall carbon nanotube composite films, Sensors and Actuators B: Chemical. 2011, vol. 152, pp. 99-106.

Su, Pi-Guey et al. A low humidity sensor made of quartz crystal microbalance coated with multi-walled carbon nanotubes/Nafion composite material films, Sensors and Actuators B: Chemical. 2006, vol. 115, pp. 338-343.

Jiang, Wei Fen et al. Resistive humidity sensitivity of arrayed multi-wall carbon nanotube nests grown on arrayed nanoporous silicon pillars, Sensors and Actuators B. 2007, vol. 125, pp. 651-655.

Ghahremanpour, M. et al. Humidity sensing properties of sprayed thin film MWCNT-PVP composites, IEEE. 2011, 978-1-4244-9289-3/11, 4 pages.

Benchirouf, A. Humidity Sensitivity of Thin Films based dispersed Multi-Walled Carbon Nanotubes, IEEE. 2013, 978-1-4673-6457-7/13, 5 pages.

(56) References Cited

OTHER PUBLICATIONS

Gamble, John et al. A Reassessment of Mercury in Silastic Strain Gauge Plethysmography for Microvascular Permeability Assessment in Man, Journal of Physiology. 1993, vol. 464, pp. 407-422.

Yan, Chaoyi et al. Highly Stretchable Piezoresistive Graphene—Nanocellulose Nanopaper for Strain Sensors, Advanced Materials. 2014 Material Views, vol. 26, pp. 2022-2027.

Xiao, Xu et al. High-Strain Sensors Based on ZnO Nanowire/Polystyrene Hybridized Flexible Films, Advanced Materials. 2011 Material Views, vol. 23, pp. 5440-5444.

Jing, Zhao et al. Review of graphene-based strain sensors, Chinese Physical Society and IOP Publishing Ltd. 2013, vol. 22, No. 5, (057701) 10 pages.

Herrmann, J. et al. Nanoparticle films as sensitive strain gauges, Applied Physics Letters. 2007, vol. 91 (183105), 4 pages.

Xu, Feng et al. Highly Conductive and Stretchable Silver Nanowire Conductors, Advanced Materials. 2012 Material Views, DOI: 10.1002/adma.201201886, 6 pages.

Sayago, I. et al. Carbon Nanotube-based SAW sensors, Spanish Conference on Electron Devices. 2013, pp. 127-130. Citation page retrieved online [Nov. 2, 2016] retrieved at: <http://www.itefi.csic.es/en/publicaciones/carbon-nanotube-based-saw-sensors>.

Kang, Inpil eta I. A carbon nanotube strain sensor for structural health monitoring, Institute of Physics Publishing, Smart Materials and Structures, 2006, vol. 15, pp. 737-748.

Cai, Le et al. Super-stretchable, Transparent Carbon Nanotube-Based Capacitive Strain Sensors for Human Motion Detection, Scientific Reports. Oct. 25, 2013, vol. 3, No. 3048, 9 pages.

Cochrane, Cédric et al. Design and Development of a Flexible Strain Sensor for Textile Structures Based on a Conductive Polymer Composite, Sensors. 2007, vol. 7, pp. 473-492.

Shin, Min Kyoon et al. Elastomeric Conductive Composites Based on Carbon Nanotube Forests, Advanced Materials. 2010 Material Views, vol. 22, pp. 2663-2667.

Weng, Wei et al. A Gum-Like Lithium-Ion Battery Based on a Novel Arched Structure, Advanced Materials. 2015 Material Views, DOI: 10.1002/adma.201405127, 7 pages.

Zhang, Zhitao et al. Superelastic Supercapacitors with High Performances during Stretching, Advanced Materials. 2014 Material Views, DOI: 10.1002/adma.201404573, 7 pages.

Li, Xiao et al. Stretchable and highly sensitive graphene-on-polymer strain sensors, Scientific Reports. Nov. 16, 2012, vol. 2, No. 870, 6 pages.

Levin, Z. S. et al. Flexible latex—polyaniline segregated network composite coating capable of measuring large strain on epoxy, IOP Publishing, Smart Materials and Structures. 2013, vol. 22, No. 015008, 10 pages.

Park, Cheol et al. Aligned Single-Wall Carbon Nanotube Polymer Composites Using an Electric Field, Journal of Polymer Science: Part B: Polymer Physics. 2006, vol. 44, 13 pages.

Slobodian, P. et al. A Highly-Deformable Composite Composed of an Entangled Network of Electrically-Conductive Carbon-Nanotubes Embedded in Elastic Polyurethane. Journal Carbon. 2012, vol. 50 Issue 10, pp. 3446-3453.

Tadakaluru, Sreenivasulu et al. Stretchable and Flexible High-Strain Sensors Made Using Carbon Nanotubes and Graphite Films on Natural Rubber, Sensors. 2014, vol. 14, pp. 868-876.

Hu, Ning et al. Investigation on sensitivity of a polymer/carbon nanotube composite strain sensor, Journal Carbon. 2010, vol. 48, pp. 680-687.

Park, Yong Tae et al. Carbon Nanotube-Based Multilayers, Multilayer Thin Films: Sequential Assembly of Nanocomposite Materials, Second Edition. Wiley-VCH Verlag GmbH & Co. KGaA. 2012, Chapter 24, 18 pages.

* cited by examiner

COMPOSITE MEMBRANE, BIOSENSOR, AND PREPARATION METHODS THEREOF

FIELD

The present application relates to a biosensor, and in particular, to a composite membrane, a biosensor, and preparation methods thereof.

BACKGROUND

The application of attachable and wearable sensors has drawn extensive attention from the research community, mainly owing to the requirement for monitoring health status of humans. Ideal sensors should have high sensitivity, the capability of fast response, low costs, high reliability at the same time, and can be produced into different shapes, sizes, and geometries. In the design of a health monitoring system, the capability of deforming biosensors in response to motions such as stretching, bending, folding, and twisting is of high importance. Recently, researchers have made enormous efforts to design motion biosensors having functions of sensing breathing or joint and muscular motions. These precious research results have been widely applied to fields, for example, biomedical clothes, robotic systems, and human motion detection.

Conventional metal-based strain gauges are unable to operate at high strain levels (more than 5%), and as a consequence, they cannot efficiently fulfill requirements for biological motion detection and wearable electronic products. The previously mercury-based strain gauges, always used in biological measurement, have toxicity and limited strain performance. Based on the above, sensors that can be used for monitoring biological motion and not only can detect high strains but also have high sensitivity need to be found, so as to fulfill the development requirements of wearable electronic products.

SUMMARY

A technical problem to be resolved by some embodiments of the present application is: to compensate for drawbacks of the foregoing prior art, a composite membrane, a biosensor, and preparation methods thereof are provided, where the prepared composite membrane is applied to the biosensor for detecting high strains, and has high sensitivity.

The technical problem of the embodiments of the present application is solved through the following technical solution:

A method for preparing a composite membrane, comprising the following steps: S1, preparing a nanocarbon material into a 0.5 to 20 wt % nanocarbon material dispersion liquid, wherein the nanocarbon material is a carbon nanotube or graphene; S2, preparing a moldable and plastic material; S3, wetting the plastic material by using the nanocarbon material dispersion liquid, stretching the plastic material along a first direction, and then folding the plastic material towards a second direction, wherein the second direction is opposite to the first direction, and repeating the stretching and folding process for 500 to 1,000 times; and S4, drying the plastic material processed in step S3 at a temperature ranging from 20 to 35° C., so as to prepare a composite membrane compounded by the plastic material and the nanocarbon material.

A composite membrane prepared according to the above preparation method.

A biosensor, comprising the above composite membrane, a first thin membrane, a second thin membrane, a first electrode wire, and a second electrode wire; wherein the composite membrane is provided on the first thin membrane; two ends of the composite membrane are respectively attached to the first electrode wire and the second electrode wire; and the second thin membrane is covered on a surface of the composite membrane.

A method for preparing a biosensor, comprising the following steps: P1, preparing a composite membrane according to the above preparation method; P2, positioning the composite membrane on a first thin membrane, and respectively attaching a first electrode wire and a second electrode wire to two ends of the composite membrane; and P3, covering a second thin membrane on a surface of the composite membrane, and drying at a temperature ranging from 20 to 35° C.

Compared with the prior art, beneficial effects of the embodiments of the present application are:

In the process of preparing the composite membrane of the present application, a moldable and plastic material is used as a carrier; after the carrier is wetted by using a dispersion liquid of a nanocarbon material, for example, carbon nanotubes (CNTs) or graphene, by means of multiple stretching and folding processes, the nanocarbon material is uniformly distributed and arranged regularly inside the entire plastic material in a stretching strain direction. Upon verification, when the prepared composite membrane is applied to a sensor, the sensor may detect strains at least up to 200% and may detect strains as high as 530%. The sensor further may have high sensitivity with a gauge factor ranging from 12 to 25. In addition, the sensor may have a fast resistance response and high durability. In addition, when the nanocarbon material is CNTs, because the composite membrane comprises the CNTs, the composite membrane may monitor humidity changes, and when the composite membrane is applied to a biosensor, the biosensor may detect motion as well as human breathing. In the present application, by means of multiple stretching and folding processes, a nanocarbon material is uniformly and regularly arranged and distributed inside an entire plastic material, so that performance may be not affected owing to limitation of the plastic material. The biosensor of the present application may be widely applied to the field of human motion detection and breathing monitoring.

DETAILED DESCRIPTION

Figure 1:
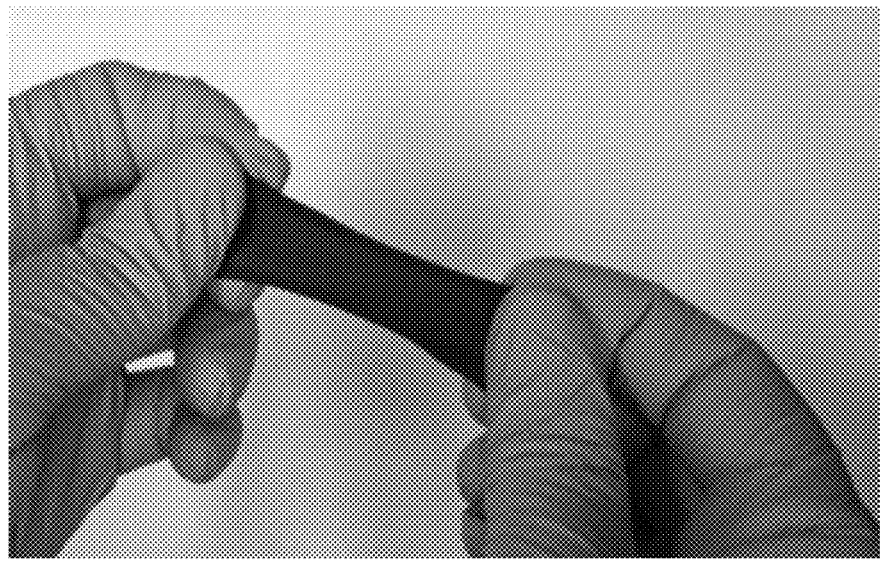
FIG. 1 is a picture of a composite membrane of an embodiment of the present application.

The present application is further described in detail below in combination with specific embodiments and with reference to the accompanying drawings.

The embodiments of the present application provide a method for preparing a composite membrane, comprising the following steps:

S1, preparing a nanocarbon material into a 0.5~20 wt % nanocarbon material dispersion liquid. The nanocarbon material is carbon nanotubes or graphene.

In the step, the dispersion liquid of the carbon nanotubes or graphene can be prepared in multiple manners, for example: by means of a mechanical dispersion method, a surface chemical covalent modification dispersion method or a non-covalent modification dispersion method of a surfactant. Preferably, the dispersion liquid is prepared by using a nanocarbon material and a surfactant; in this way, a dispersion effect is good, and a structure of the nanocarbon material is not damaged. When carbon nanotubes are selected as the nanocarbon material, the carbon nanotubes may be single-walled carbon nanotubes or multiwalled carbon nanotubes. In dispersion, a block polyether macromolecular surfactant may be selected as the surfactant, and is mainly formed by polyoxyethylene (PEO) as hydrophilic part and polyoxypropylene (PPO) as hydrophobic part. Multiwalled carbon nanotubes (MWCNT) are selected as the nanocarbon material in one specific embodiment, and a Pluronic F-127 water solution is selected as the surfactant. In preparation, an MWCNT solution may be dispersed in the surfactant water solution, then performing sonication to the mixed solution, so as to make MWCNTs dispersed to a greatest extent, and finally prepare the carbon nanotube dispersion liquid. By means of concentration and volume adjustment of the MWCNT solution and the surfactant water solution, weight percentage of the carbon nanotubes in the carbon nanotube dispersion liquid is 0.5 to 20%.

Preferably, weight percentage of the carbon nanotubes in the prepared carbon nanotube dispersion liquid is 3.5 wt % to 6 wt %. Within the concentration range, CNT content is sufficient, and sensing resistance functions based on only a connection of the carbon nanotubes, and water molecules do not contribute in transferring electrons, so that resistance follows a linear change trend versus strains. At the same time, the CNT content is not excessive, thereby avoiding a decrease of flexibility and scalability of the subsequently formed composite membrane, and preventing an excessively hard composite membrane from being prepared.

Further preferably, in ultrasonic dispersion, the mixed solution is positioned in an ice-water environment; after 35 to 45 min of sonication, the mixed solution stays in the ice-water environment for 5 to 15 min, and then sonication is performed for 35 to 45 min. Sonication is performed in an ice-water environment and a duration for staying in the ice-water environment in the interval period of the sonication is set, so as to avoid a temperature increase of the mixed solution owing to the sonication, and ensure that a temperature of the mixed solution is always kept low during the dispersion, and therefore the subsequently prepared composite membrane has good performance.

S2, preparing a moldable and plastic material.

In the step, a plastic material is prepared to facilitate subsequent stretching and folding, and is also advantageous to uniform dispersion of the nanocarbon material solution. Available plastic materials can all be applied thereto. Preferably, a chewed chewing gum is used as the plastic material, and has a low cost and is easily obtained.

When a chewing gum is used as the plastic material, a chewed chewing gum is positioned in a mixed solution prepared by ethanol and distilled water and is shaken for 10 to 14 h; then the chewing gum is washed, and is air-dried at a temperature ranging from 20 to 35° C. The washed and air-dried chewing gum is used as the plastic material for subsequent use.

S3, wetting the plastic material by using the dispersion liquid; stretching the plastic material along a first direction, and then folding the plastic material towards a second direction, where the second direction is opposite to the first direction; and repeating the stretching and folding process for 500 to 1,000 times.

In the step, the plastic material is wetted by using the nanocarbon material dispersion liquid prepared in step S1, where the plastic material is preferably a chewing gum. After the plastic material is stretched towards a direction (the first direction), the plastic material is folded towards an opposite direction (the second direction), and the stretching and folding process is repeated for 500 to 1,000 times to implement uniform distribution. Specifically, for example, a left end of a chewing gum is fixed, and the chewing gum is stretched towards the right, and then a right end of the chewing gum is folded towards a left direction. Next time, the chewing gum is stretched towards the right and is folded towards the left; the stretching direction each time is a same direction and the folding direction each time is also a same direction, and the two directions are opposite to each other, so that the nanocarbon material is uniformly and regularly arranged and distributed in the chewing gum.

S4, drying the plastic material processed in step S3 at a temperature ranging from 20 to 35° C., so as to prepare a composite membrane compounded by the plastic material and the nanocarbon material.

Figure 2:
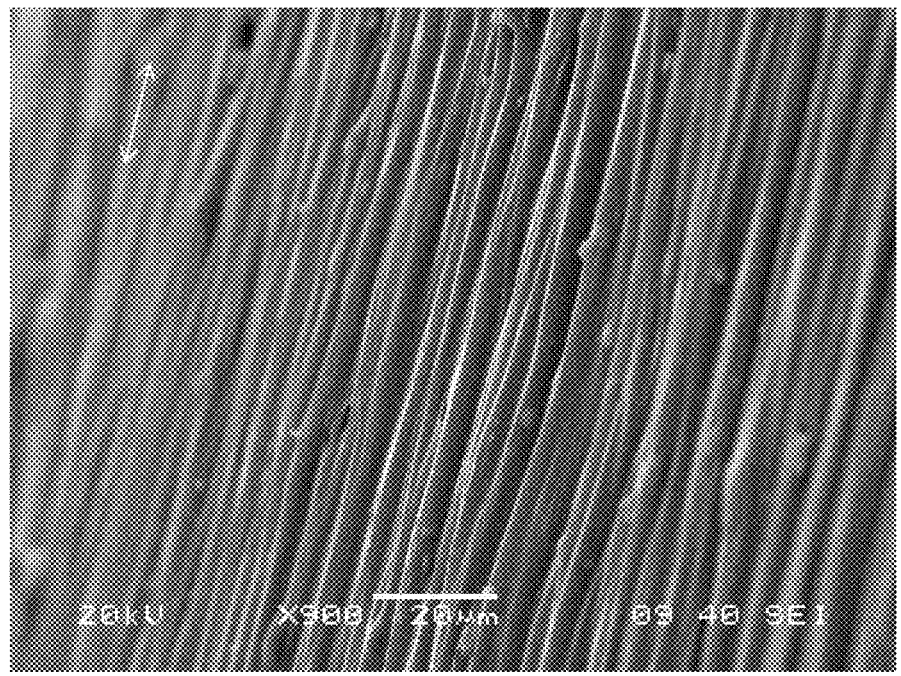
FIG. 2 is a schematic diagram of a laminated structure in a composite membrane of an embodiment of the present application.

As shown in FIG. 1, FIG. 1 is a schematic structural diagram of the prepared composite membrane compounded by the CNTs and the chewing gum. As shown in FIG. 2, FIG. 2 is an SEM image thereof, and arrow head in FIG. 2 shows stretching direction. From FIG. 2, it can be known that the chewing gum embedded with the CNTs presents a laminated structure of regular arrangement.

The composite membrane prepared in the present specific embodiment uses a moldable plastic as a basal body, and a nanocarbon material, for example, carbon nanotubes or graphene is added into the basal body. By means of stretching and folding for multiple times, the CNTs or graphene is regularly and uniformly arranged inside the plastic along a stretching strain direction, so that when the membrane structure is applied to a sensor, the sensor may detect high strains and has high sensitivity. In addition, the sensor has a fast resistance response and high durability.

Figure 3:
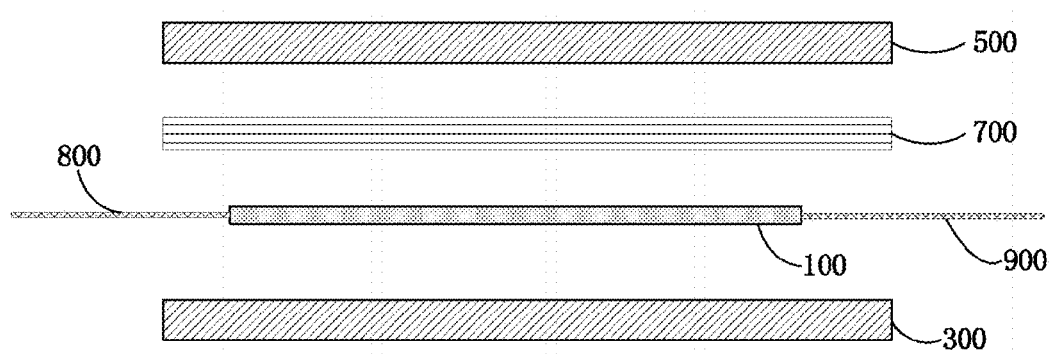
FIG. 3 is a schematic structural diagram of a biosensor of an embodiment of the present application.

The present specific embodiment further provides a biosensor, as shown in FIG. 3, comprising the above prepared composite membrane 100, a first thin membrane 300, a second thin membrane 500, a first electrode wire 800, and a second electrode wire 900. The composite membrane 100 is provided on the first thin membrane 300; two ends of the composite membrane 100 are respectively attached to the first electrode wire 800 and the second electrode wire 900. The second thin membrane 500 is covered on a surface of the composite membrane 100. Preferably, the biosensor further comprises a protection layer 700, which is provided between the second thin membrane 500 and the composite membrane 100, and is covered on the surface of the composite membrane 100. The protection layer 700 may be a silicone elastomer. The composite membrane 100 can be protected by the protection layer 700, so that the composite membrane 100 performs measurement and monitoring more stably.

As stated below, strain detection performance, resistance response performance, and humidity test performance of the composite membrane that is compounded by MWCNTs and a chewing gum and is prepared in the foregoing preparation process are verified by means of specific experimental examples.

Preparation of an MWCNT/chewing gum membrane: MWCNTs with different weight percentages: 2, 4, 6, and 8 wt % MWCNTs are added to 2 wt % water solution of poloxamer 407 (Pluronic F-127); by means of volume adjustment, carbon nanotube dispersion liquids with weight percentages: 1.9, 3.7, 5.55, and 7.27 wt % carbon nanotubes are prepared. The MWCNT solutions are sonicated by using a probe Q 700 sonicator at power of 100 W for 2 h (6 s on and 1 s off). The sonication is performed under an ice-water condition, and therefore the temperature is always kept low during the sonication. After 30 min of sonication each time, the solutions are kept in ice-water for 10 min and then sonicated again for another 30 min. Energy dispersive spectroscopy (EDX) analysis is performed on the dispersion liquids obtained after the sonication, and no titanium element peak is observed, which indicates that there is no release of the probe material into the MWCNT dispersion liquids in the sonication process, and the sonication process is safe.

A chewing gum is chewed for 30 min and washed with ethanol and distilled water by shaking for 12 h; then, the chewing gum is left in room temperature for 12 h to let excess water evaporate and reach a stable weight after being air-dried. Note that the type of the chewing gum is not important. Experiments have been done for different chewing gums, and the result indicates that although there is a difference in Young's modulus, performances of the prepared strain sensors are same. In the experiments, Doublemint gum is used.

Then, the chewing gum is wetted by using the foregoing prepared MWCNT solutions, and the chewing gum is stretched towards a same direction and then folded towards an opposite direction. Stretching and folding are repeated for about 500 times. Finally, the chewing gum is cured at room temperature to obtain a composite membrane compounded by the MWCNTs and the chewing gum.

Preparation of a sealed chewing gum biosensor: two copper tapes with a 2 cm distance from each other are attached to a thermally cured first PDMS thin membrane. The composite membrane is positioned on the first PDMS thin membrane while two ends are respectively attached to the two copper tapes. Then a silicone elastomer base is covered on a surface of the composite membrane as a protection layer. Then a second PDMS thin membrane is positioned on the silicone elastomer. After each lamination seals the composite membrane, the sensor is dried at room temperature.

As stated above, the carbon nanotube dispersion liquids have different concentrations, and therefore corresponding different composite membrane samples can be prepared, and are respectively defined as a membrane sample 1 (1.9 wt % MWCNTs), a membrane sample 2 (3.7 wt % MWCNTs), a membrane sample 3 (5.55 wt % MWCNTs), and a membrane sample 4 (7.27 wt % MWCNTs). Correspondingly, corresponding different biosensors can be prepared, which are respectively defined as a sensor sample 1 (1.9 wt % MWCNTs), a sensor sample 2 (3.7 wt % MWCNTs), a sensor sample 3 (5.55 wt % MWCNTs), and a sensor sample 4 (7.27 wt % MWCNTs).

1. Microstructure observation

Using the membrane sample 3 as an example, the composite membrane is kept in a freezer (−80° C.) for 30 min and then broken for SEM analysis. In the analysis, a JEOL scanning electron microscope is used to perform scanning.

Figure 4:
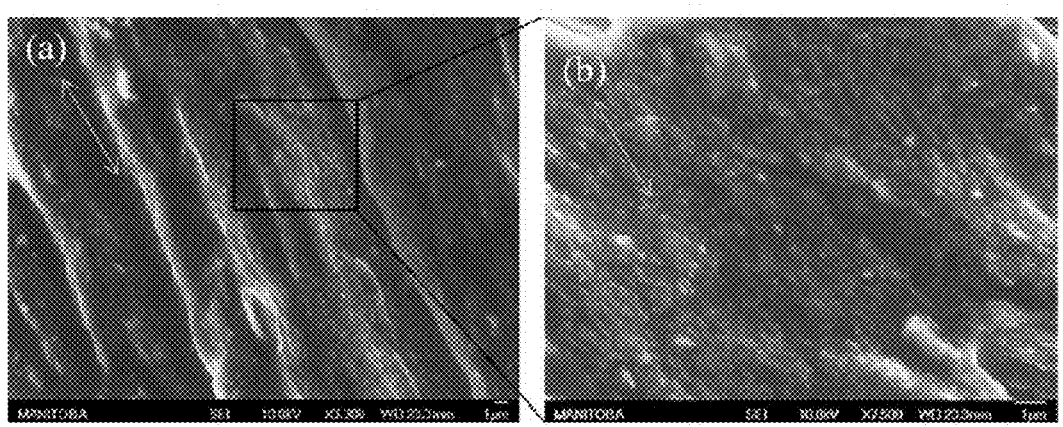
FIG. 4 is a surface SEM image of a composite membrane of an embodiment of the present application.
Figure 5:
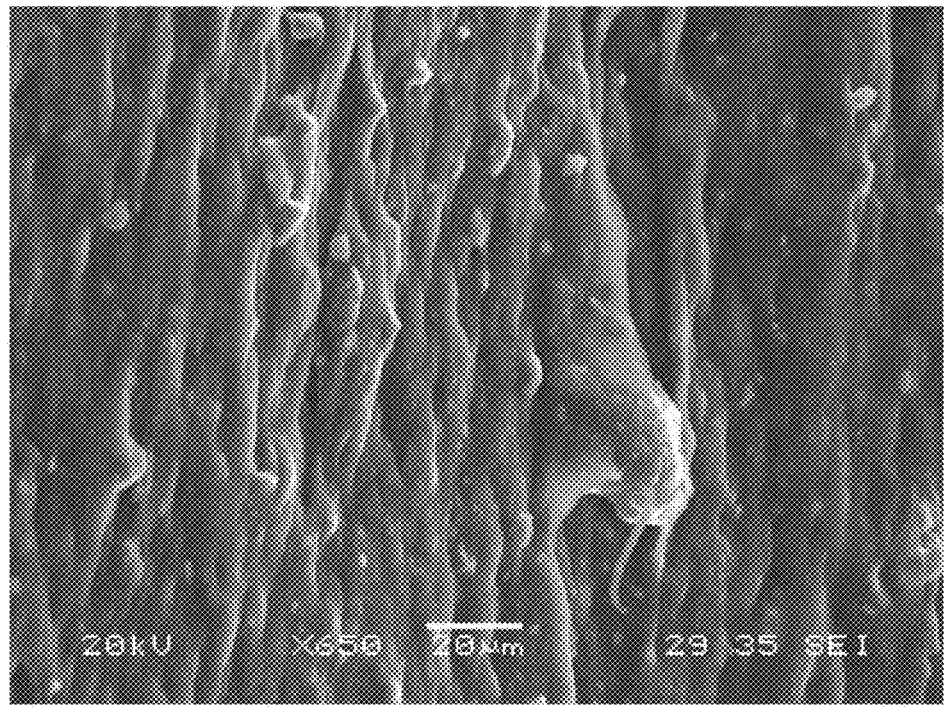
FIG. 5 is an SEM image of a composite membrane at a larger multiple of an embodiment of the present application.
Figure 6:
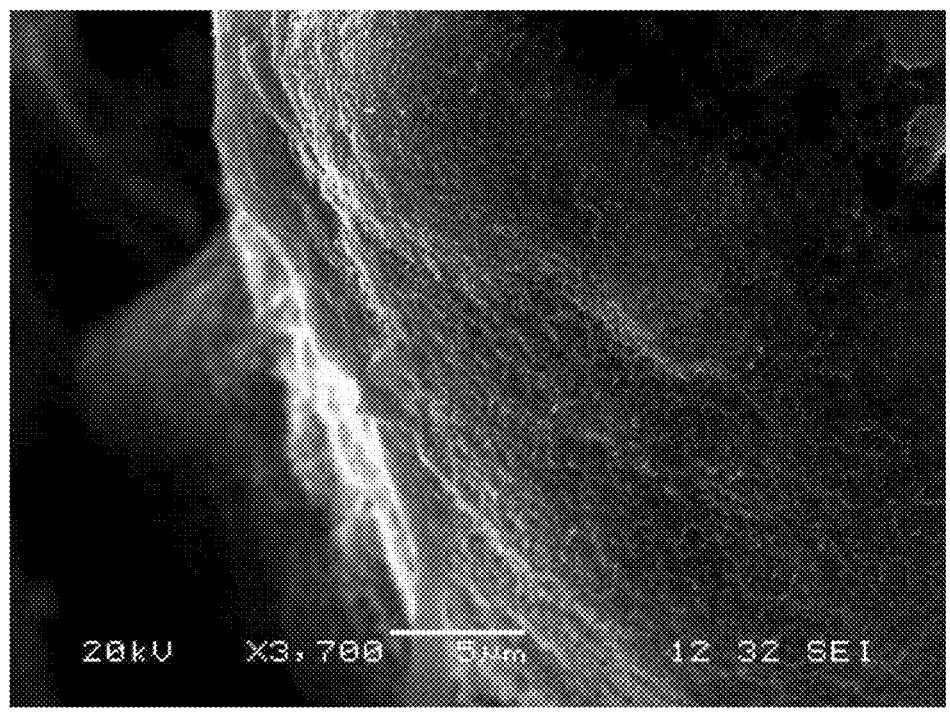
FIG. 6 is an SEM image of a chewing gum sheet for reference in an embodiment of the present application.

FIG. 4a shows a surface SEM image, which is obtained by scanning, of the composite membrane. FIG. 4b shows an SEM image of a part illustrated in a box of 4a at a large multiple. Arrow head in FIG. 4a and FIG. 4b represents stretching direction. From the drawings, it can be known that the composite membrane has a laminated structure. Stretching and folding for multiple times enables carbon nanotubes of each layer to be arranged in the stretching strain direction shown in the drawings. FIG. 5 shows an SEM image at a larger multiple obtained by scanning. From FIG. 5, it can be seen that the composite membrane has a laminated structure of regular arrangement. For comparison, FIG. 6 shows an SEM image of a chewing gum sheet obtained by arbitrarily mixing CNTs and a chewing gum. From FIG. 6, it can be known that a laminated structure of regular arrangement cannot be obtained by arbitrary mixing.

Figure 7:
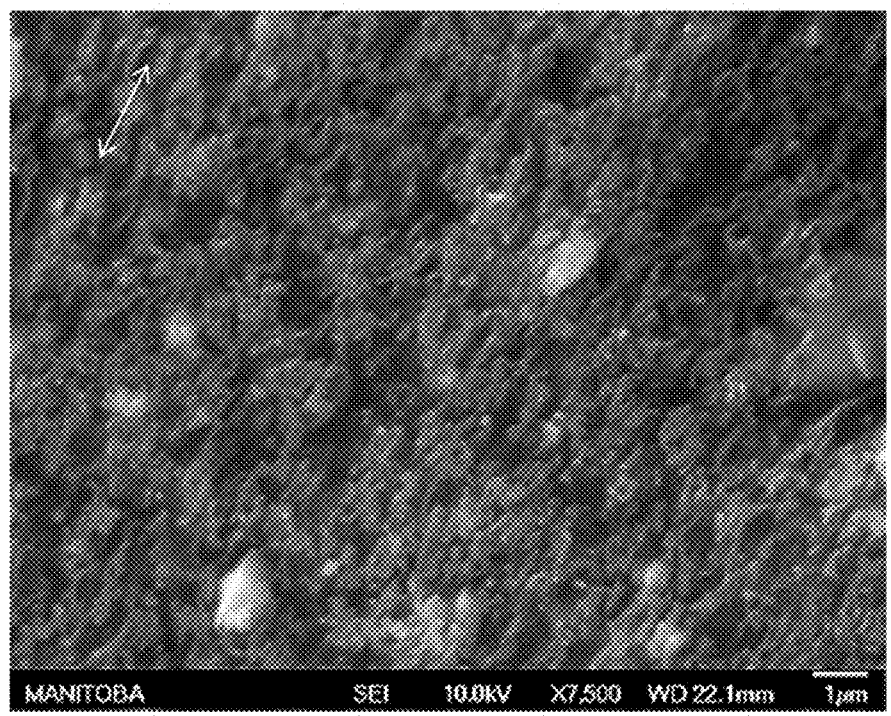
FIG. 7 is an SEM image of a composite membrane of an embodiment of the present application.

Using the sensor sample 3 as an example, an SEM image shown in FIG. 7 is obtained by scanning a surface of the sensor using an electron microscope.

2. Stability test: resilience of the composite membrane in different environments is tested.

Environment 1: using the membrane sample 3 as an example, the composite membrane is kept in both a buffer solution, of which pH is 7, and distilled water for one week. Each day in the week, the composite membrane is stretched and folded in the liquids and is kept therein for 12 h. After one week, the color of the liquids is clear, which can indicate that the CNTs are not released from the composite membrane.

Environment 2: using the membrane sample 3 as an example, the composite membrane is positioned in a container filled with water, and is shaken for 12 h in a 40° C. environment; after shaking, the color of the water does not change, which also indicates that the CNTs are not released from the composite membrane.

Based on the foregoing tests, it may be known that the attachable nature of the sensor makes it difficult to release CNTs from the chewing gum matrix in different conditions.

3. Tensile test:

By using the membrane sample 3 as an example, the composite membrane of the membrane sample 3 with a 20 mm length, a 3 mm width, and a 0.3 mm thickness is used for test. In the test, the composite membrane of the membrane sample 3 with a 20 mm length, a 3 mm width, and a 0.3 mm thickness is tested by INSTRON 5965 (Instron, Norwood, Mass., USA). A strain speed is constant at 5 mm/min. To determine the dependence of resistance R of the composite membrane on different strains, an INSTRON machine is used to perform elongation at a constant speed of 5 mm/min. At the same time, the resistance is measured by using a two-probe digital multi-meter (VICTOR 86E, digital multi-meter), and two ends of the sample are attached to the probes by means of the copper tapes.

Figure 8:
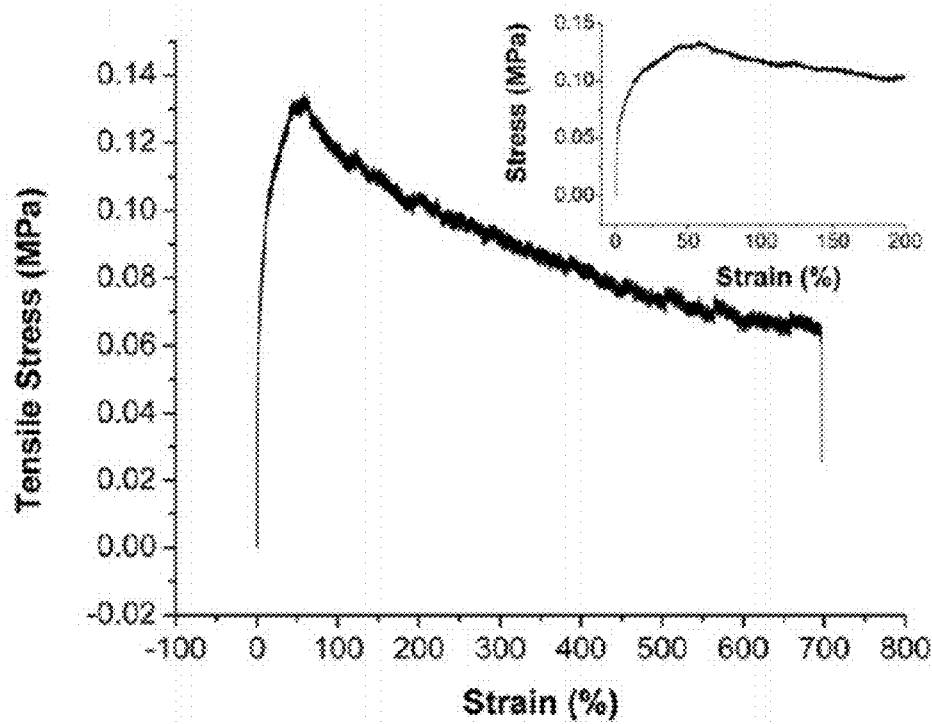
FIG. 8 is a stress-strain curve of a composite membrane of an embodiment of the present application.

To evaluate elastic properties of the composite membrane, a relationship between externally applied tensile stress and composite membrane strains is tested. A stress-strain curve (at a strain speed of 5 mm/min) during tensile loading is shown in FIG. 8. Young's modulus of the composite membrane is about 1.3 MPa, which is 6.5 times higher than a reference (a chewing gum membrane with no CNTs). An increase of Young's modulus of the composite membrane may indirectly indicate a complete penetration of MWCNTs into the chewing gum.

Figure 9:
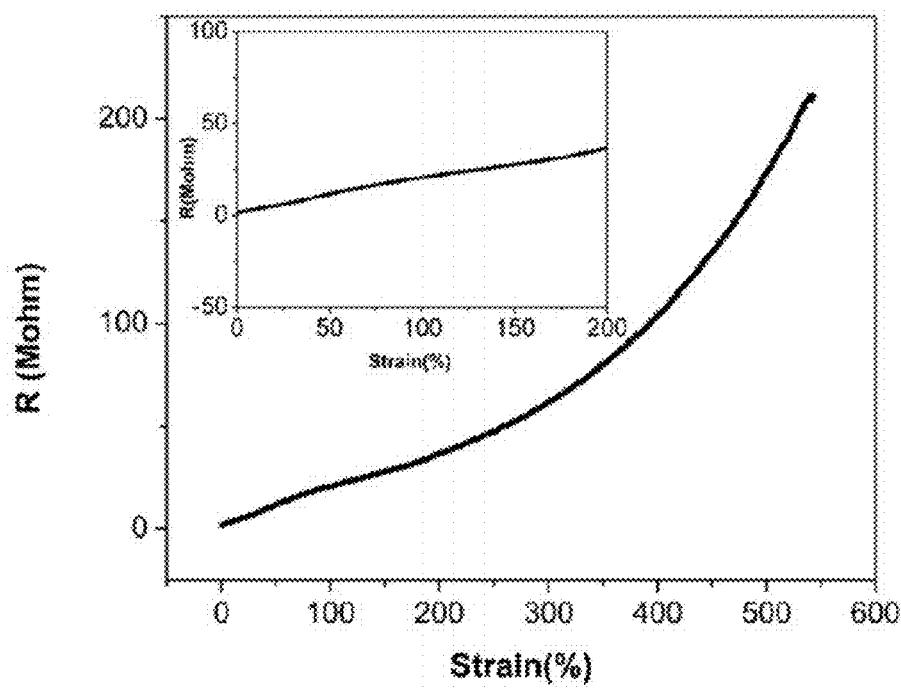
FIG. 9 is a curve of resistance variations versus strains of a composite membrane of an embodiment of the present application.

A curve of resistance variations versus strains of the composite membrane is shown in FIG. 9. A two-probe measurement technique is used to test variations of the resistance R of the composite membrane. From FIG. 9, it can be known that the resistance trend experiences an almost linear regime for strains in a range of 0 to 200%, which is quite prominent. One reason may be that for the composite membrane with a 5.55 wt % concentration of CNTs, the concentration is relatively high, and therefore a mechanism of sensing the resistance is based on only a connection of CNTs, and water molecules do not contribute in transferring electrons. The other reason may be that, in higher concentrations, CNTs are in contact and more interconnected, and therefore the resistance follows a linear trend in lower strains (the tunneling resistance would not play a role until larger levels of strains).

Figure 10:
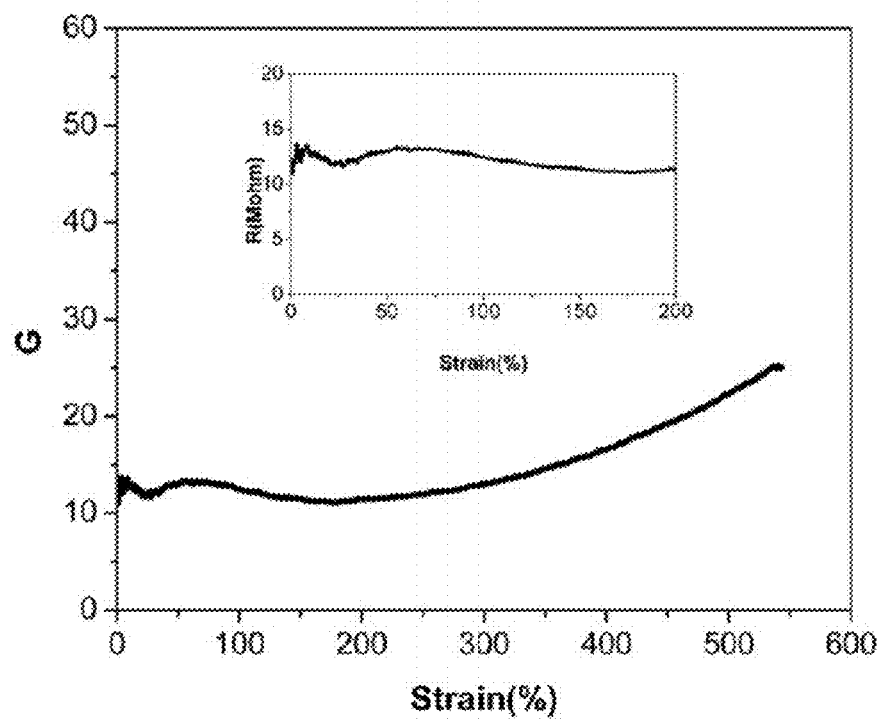
FIG. 10 is a curve of variations of a tensile gauge factor versus strains of a composite membrane of an embodiment of the present application.

A curve of variations of a tensile gauge factor G versus strains of the composite membrane is shown in FIG. 10. The gauge factor is one criterion for evaluating the sensitivity of strain sensors, and a formula is $G=(R-R_0)/R_0\varepsilon$, in which $\varepsilon$ represents the strain; R represents the resistance and $R_0$ represents the primary resistance. From FIG. 10, it can be known that when the strain is in a range of 0 to 200%, and the gauge factor of the composite membrane is almost kept at 12. Subsequently, the value of G increases with the increase of the strain. From FIG. 10, it can be known that when the strain is 200%, the gauge factor is 12, and when the strain is 530%, the gauge factor is 25.

Figure 11:
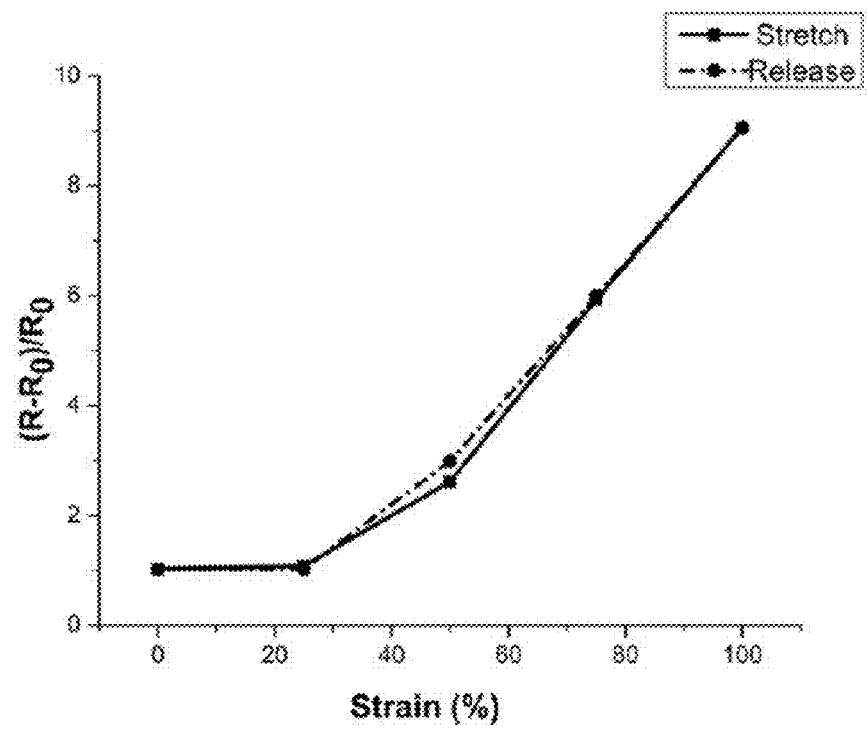
FIG. 11 is a curve of resistance variations versus strains of a composite membrane after the composite membrane is stretched and released of an embodiment of the present application.

FIG. 11 shows a curve of resistance variations versus strains of a composite membrane located between two polydimethylsiloxane substrates when the composite membrane is stretched to 100% of an initial length and then released. From FIG. 11, it can be known that the resistance of the composite membrane is almost reversible. One possible reason is that stretching and releasing for multiple times in the preparation process cause carbon nanotubes to buckle into waves. These aligned wavy bundles of MWCNTs cause larger contact areas between CNTs. These waves help the resistance response follow a linear trend in lower amplitudes (as shown in FIG. 9 and FIG. 10), since MWCNTs are still in contact with each other. After strain is further applied to the composite membrane, these wavy bundles become straighter and contact areas are smaller (since MWCNTs are still in touch, the tunneling effect does not interfere); as a result, the resistance decreases. Upon the release of the stress, the MWCNTs bundle again so that the electrical property is recovered.

Figure 12:
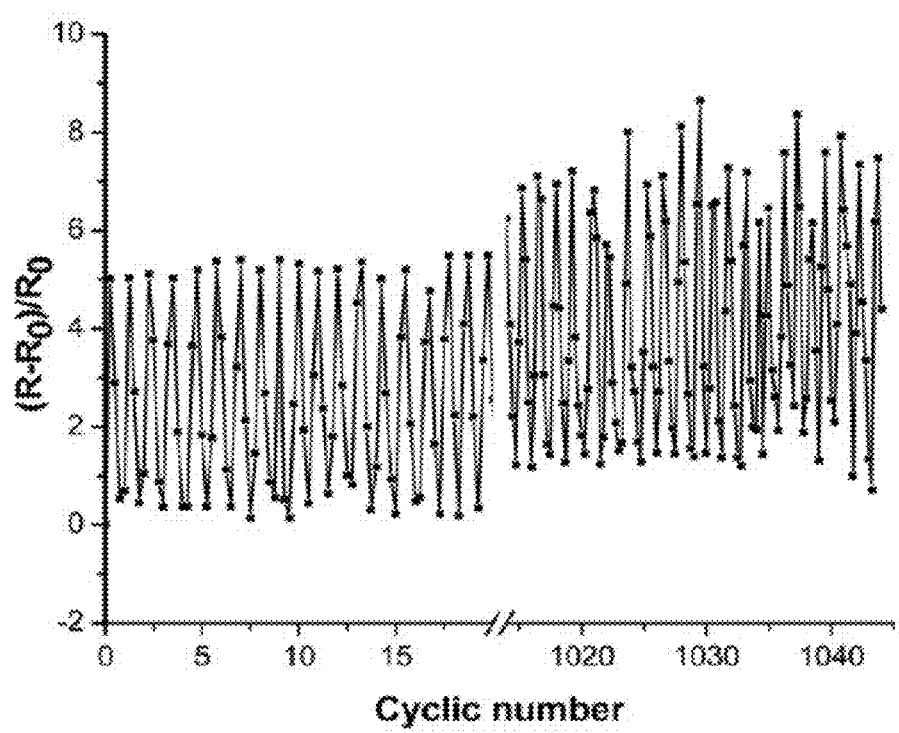
FIG. 12 is a schematic diagram of resistance variations of a composite membrane in a cyclic stretching and releasing process of an embodiment of the present application.
Figure 13:
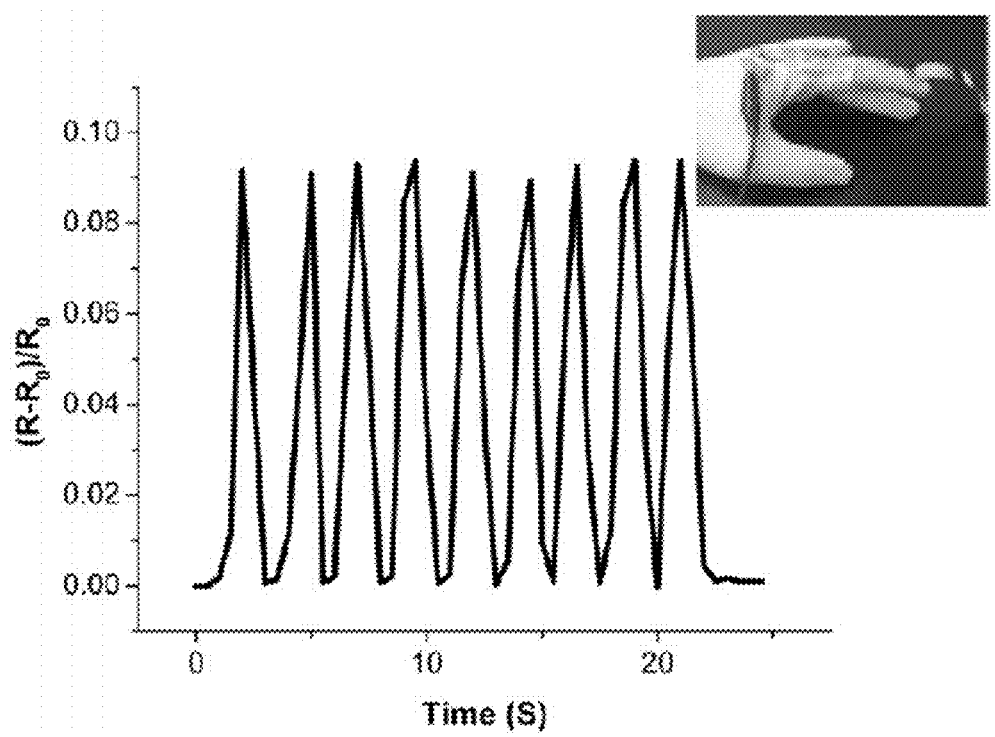
FIG. 13 is a schematic diagram of resistance variations of a composite membrane as a human finger is bent by 10° of an embodiment of the present application.
Figure 14:
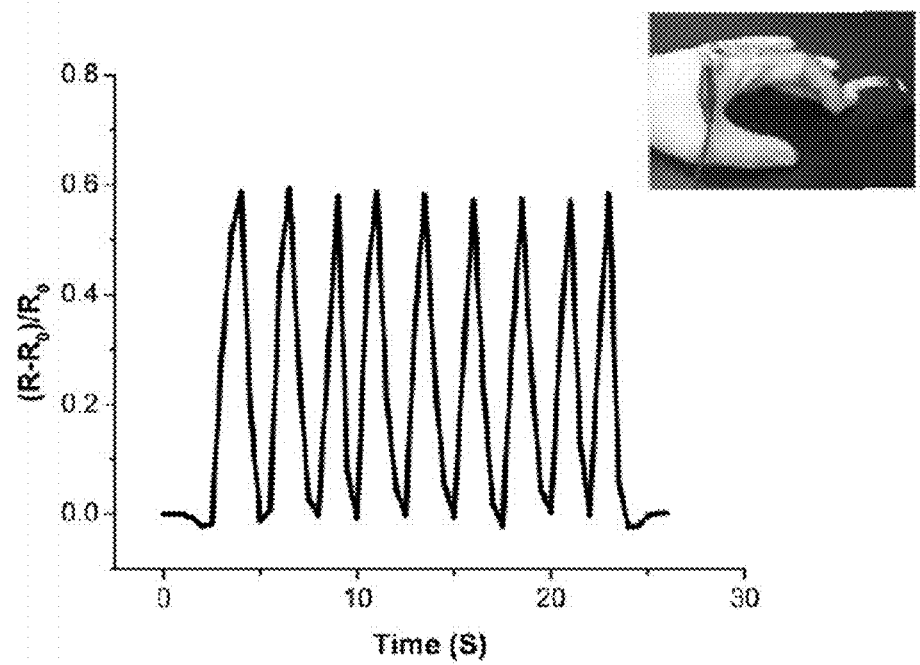
FIG. 14 is a schematic diagram of resistance variations of a composite membrane as a human finger is bent by 30° of an embodiment of the present application.
Figure 15:
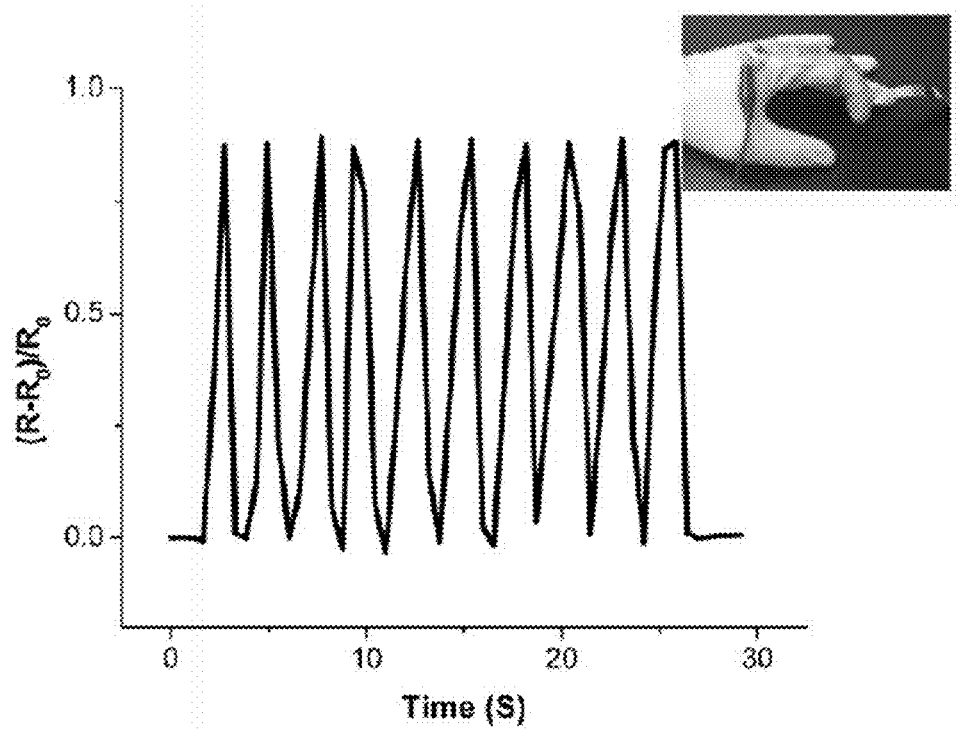
FIG. 15 is a schematic diagram of resistance variations of a composite membrane as a human finger is bent by 45° of an embodiment of the present application.

FIG. 12 is a schematic diagram of resistance variations of the composite membrane in cyclic stretching and releasing processes. During stretching, strain ranges from 0 to 50%. In each cyclic stretching and releasing process, stretching and releasing each occupy 50%. From FIG. 12, it can be known that after 1,000 cycles, the resistance only increases by 10%, and the stability of the composite membrane in the stretching process is good; in addition, in this cyclic condition, stretch and release resistances are completely controllable.

Figure 16:
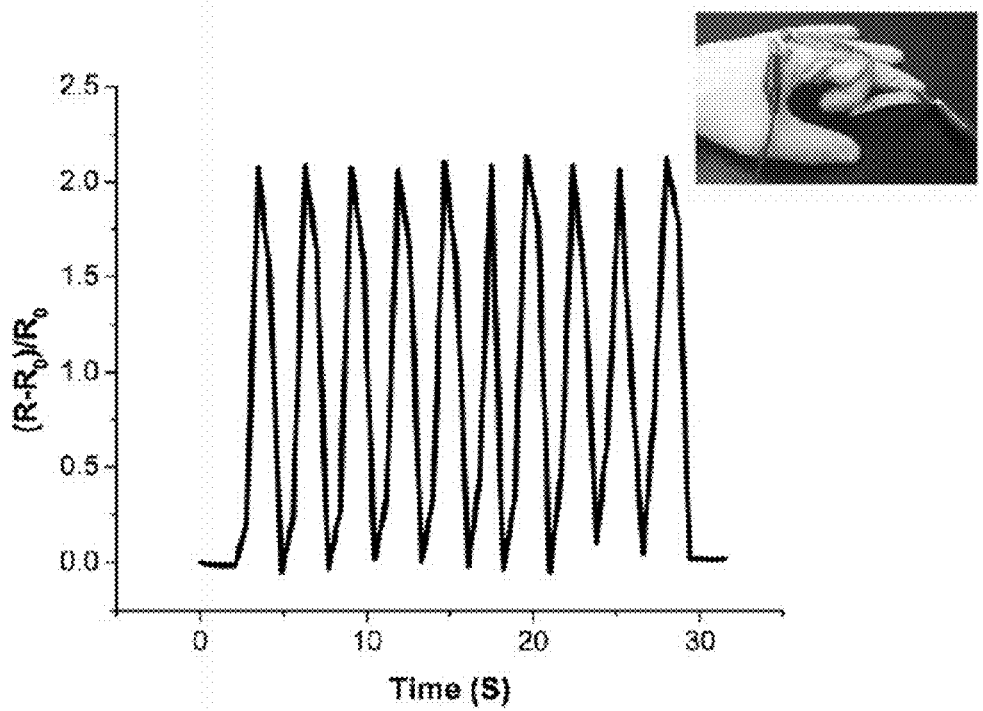
FIG. 16 is a schematic diagram of resistance variations of a composite membrane as a human finger is bent by 90° of an embodiment of the present application.

To evaluate the applicability of the composite membrane in medical devices for monitoring human motion, the composite membrane is tested as a strain sensor in different scenarios. The membrane sample 3 is sealed between two PDMS thin membranes, and then the sealed structure is attached to an index finger, and is attached to the proximal interphangeal of the index finger. FIGS. 13 to 16 respectively show the corresponding resistance variations when the finger is bent by 10°, 30°, 45°, and 90°. From FIGS. 13 to 16, it can be known that the composite membrane can efficiently monitor large and small angles. When bending angles increase from 0° to 90°, the resistance value increases as high as 200% of its initial value (FIG. 16).

To better verify the potential of the composite membrane, the membrane sample 3 is further tested by being attached on a throat; in the test, the membrane sample 3 is sealed between the two PDMS thin membranes, and then the sealed structure is attached to a throat corresponding to a human thyroid cartilage; the composite membrane is attached to a copper tape, and the copper tape is connected to a digital multi-meter.

Figure 17:
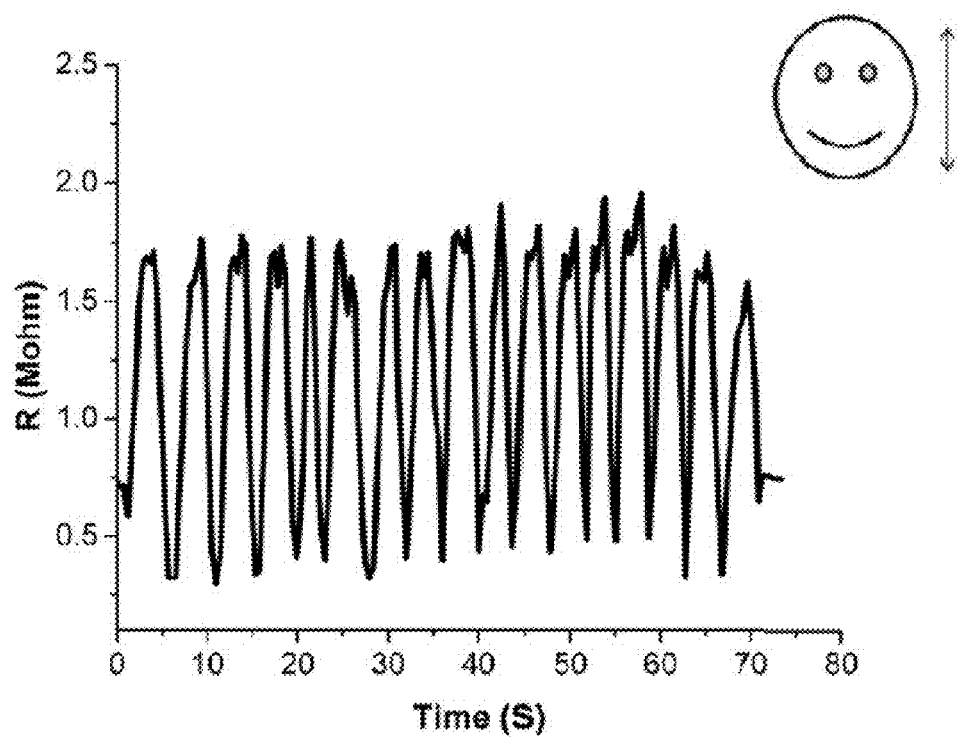
FIG. 17 is a schematic diagram of resistance variations of a composite membrane as a human head moves up and down of an embodiment of the present application.
Figure 18:
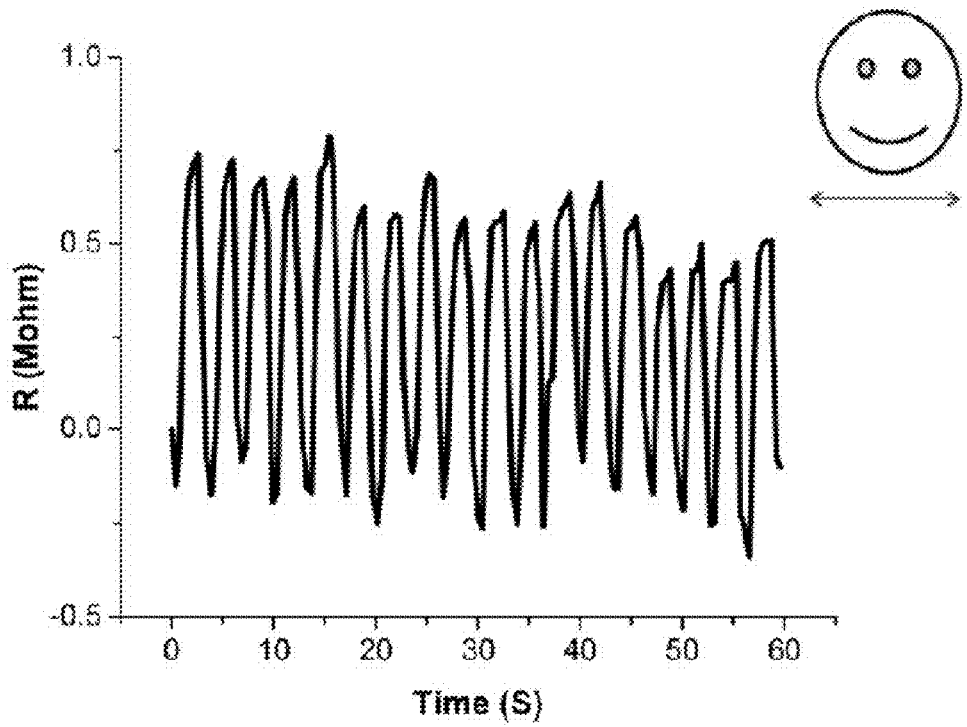
FIG. 18 is a schematic diagram of resistance variations of a composite membrane as a human head moves left and right of an embodiment of the present application.
Figure 19:
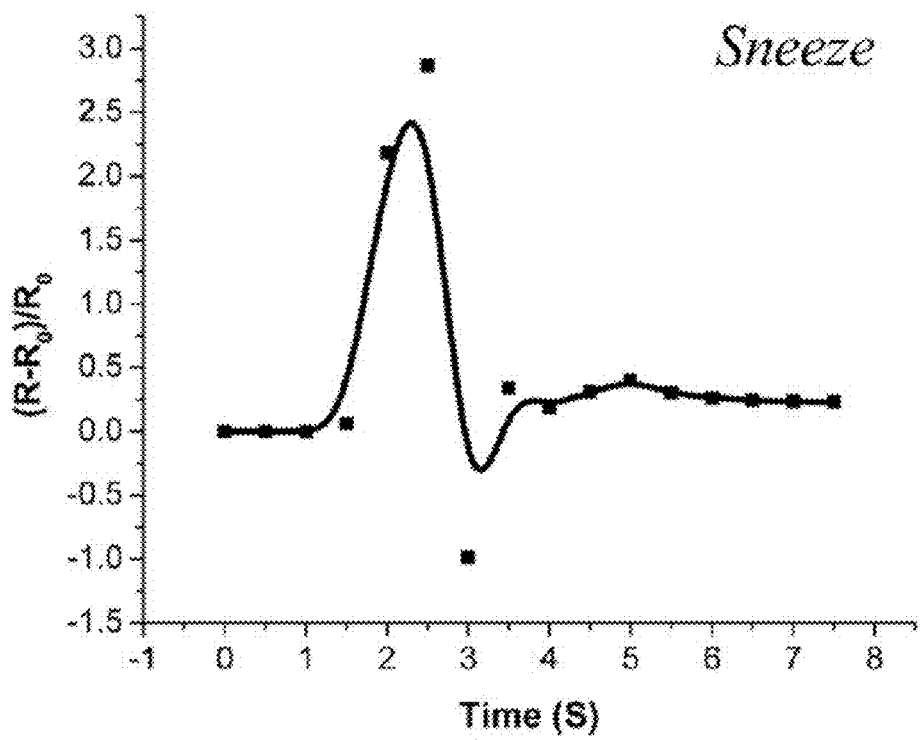
FIG. 19 is a schematic diagram of resistance variations of a composite membrane as a human sneezes of an embodiment of the present application.
Figure 20:
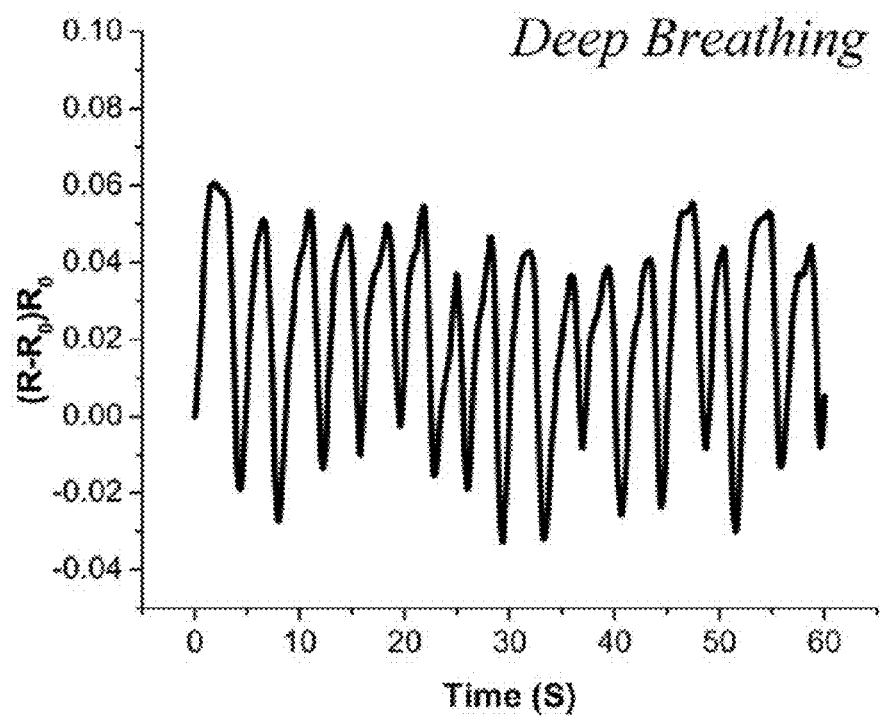
FIG. 20 is a schematic diagram of resistance variations of a composite membrane when deep breathing is monitored of an embodiment of the present application.
Figure 21:
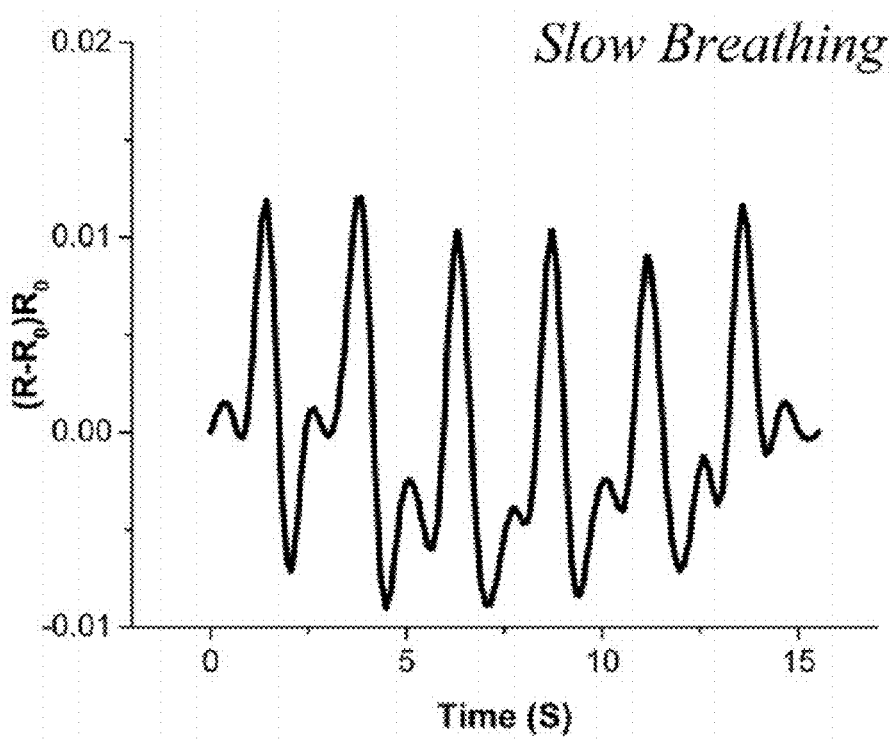
FIG. 21 is a schematic diagram of resistance variations of a composite membrane when slow breathing is monitored of an embodiment of the present application.

FIG. 17 and FIG. 18 respectively illustrate resistance responses of the composite membrane located at the throat upon up-down and left-right movements of a head. Upon muscular motion of a neck, small stretching is performed on the composite membrane, thereby causing resistance variations. As shown in FIG. 19, a sneeze causes muscular motion, and further causes resistance variations of the composite membrane. FIG. 20 and FIG. 21 respectively show recorded curves of resistance variations when deep breathing and slow breathing are monitored. From the drawings, it can be known that the composite membrane has high sensitivity and accuracy, and can monitor extremely sensitive and subtle biological motion.

Figure 22:
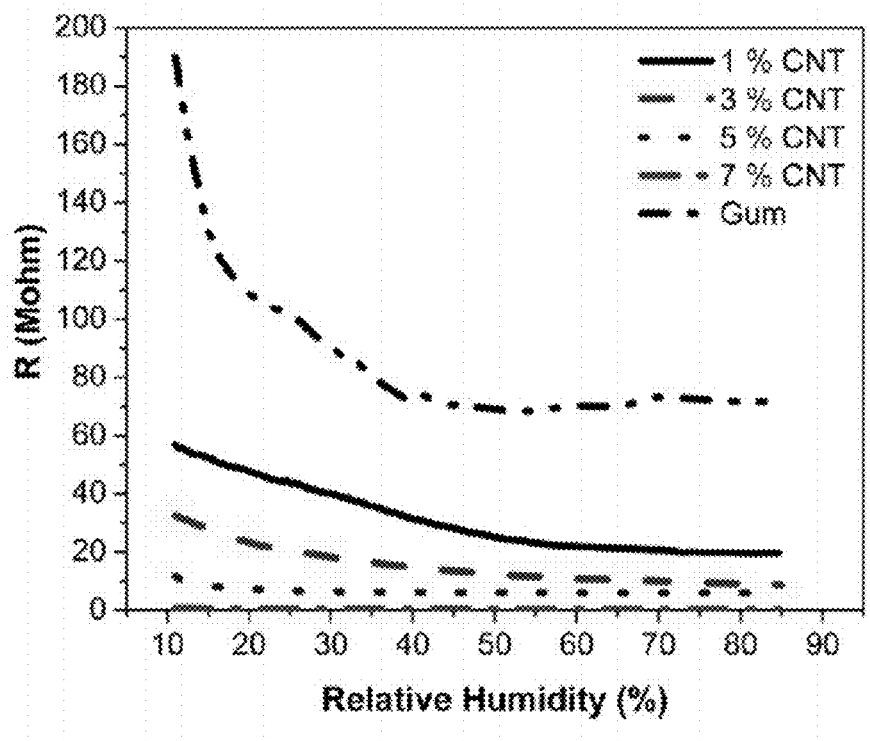
FIG. 22 is a schematic diagram of resistance variations of each sample membrane upon an increase of relative humidity of an embodiment of the present application.

4. Humidity test:

Sample membranes with a same size (a 20 mm length, a 3 mm width, and a 0.3 mm thickness) and different CNT concentrations are provided. A two-point probe machine is used to measure the resistance; the sample membrane is kept in a closed empty container in which the humidity is changed by using a humidifier and measured by using a humidity meter (CEM, DT-625). As shown in FIG. 22, FIG. 22 is a schematic diagram of resistance variations of each sample membrane upon an increase of a relative humidity. From FIG. 22, it can be known that as the humidity increases, the resistance decreases exponentially for composite membranes with lower CNT concentrations. With an increase in the CNT concentration in the composite membrane, the resistance decreases with smaller slopes in which, at 7% CNT concentration (near a percolation threshold), the resistance remains unchanged within the entire humidity range. One possible reason is that in lower CNT concentrations, ions in water can contribute in transferring electrons, and while with an increase of CNT concentrations, the CNT junction resistance dominates the humidity sensing.

Figure 23:
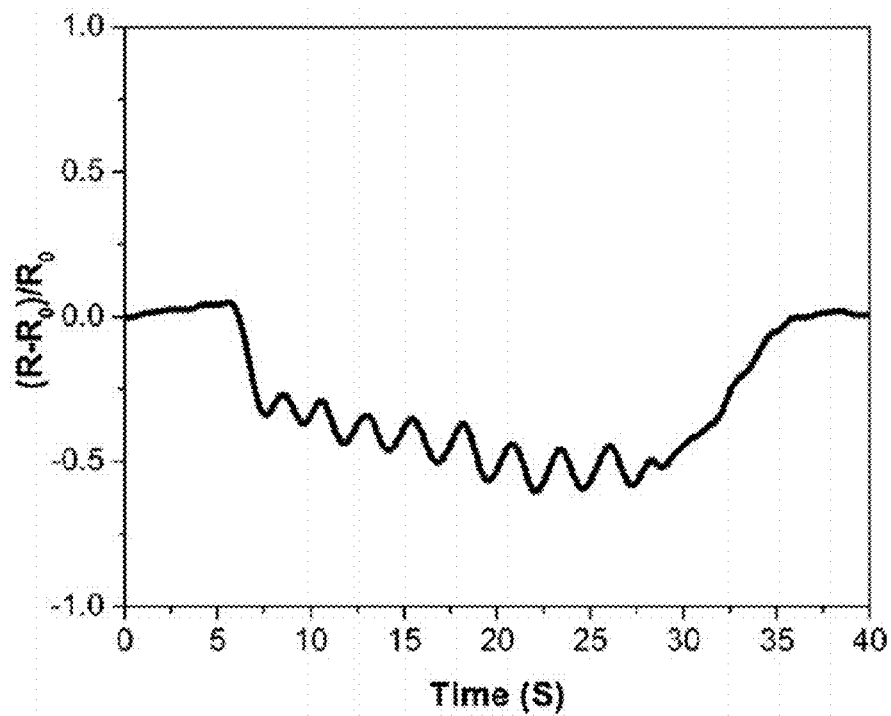
FIG. 23 is a schematic diagram of resistance variations of a composite membrane when human breathing is monitored of an embodiment of the present application.

As shown in FIG. 23, FIG. 23 is a schematic diagram of resistance variations when human breathing is monitored. In the test, a human nose is 3 cm away from the composite membrane, and in normal cases, the human breathes for 20 s each time while the resistance variations in the process are monitored. After a humidity source is removed from the composite membrane, the composite membrane can rapidly respond to humidity changes. On such basis, the composite membrane may be used to count the number of breaths of a human. Moreover, after the humidity source is removed from the composite membrane, the value of the resistance returns to the initial value (recovery of the resistance), indicating that the process of sensing humidity is fully reversible.

For the humidity test, it is likely that p-type CNTs turns into n-type CNTs when water vapors increase, so that the composite membrane may be used as a humidity sensing material. However, according to the foregoing humidity test, it indicates that the composite membrane has high sensitivity and may quickly respond to humidity changes.

Figure 24:
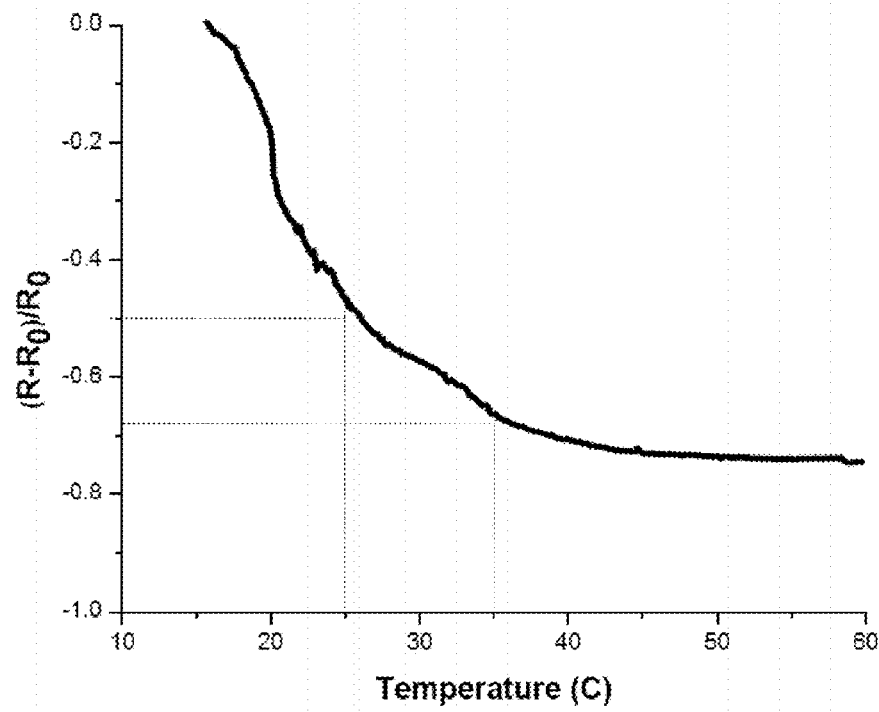
FIG. 24 is a schematic diagram of resistance variations of a composite membrane upon temperature changes of an embodiment of the present application.

5. Temperature dependency test:

The membrane sample 3 with a 5.55% CNT concentration (a 20 mm length, a 3 mm width, and a 0.3 mm thickness) is attached to the outside of a container filled with water. The container is placed on a plate heater with a magnetic bar rotating therein. In the process of an increase of the temperature of the heater, a two-point probe machine is used to measure the resistance of the composite membrane. FIG. 24 is a schematic diagram of resistance variations of the composite membrane upon temperature changes. From FIG. 24, it can be known that when the temperature increases, the resistance decreases, and when the temperature increases from 25° C. to 35° C., the resistance decreases by 10%. One possible reason for the change is that, with the increase of the temperature, the composite membrane becomes softer, and therefore carbon nanotubes therein are more relaxed and can transfer electrons more easily.

The test result indicates that the composite membrane can quickly acclimate to the environment temperature. When the external temperature increases from 25° C. to 35° C., the resistance decreases only slightly (decreases by 10% only). Therefore, when the composite membrane is used as a biosensor to monitor motion of a living body, the temperature of the living body does not affect the effectiveness of the composite membrane.

6. Conductivity test:

The conductivity of each sample composite membrane (a 13 mm length, a 7 mm width, and a 0.3 mm thickness) is measured by using a four-point probe method. First, a sheet resistance $R_s$ is measured by using a four-point probe machine, and then according to the sheet resistance $R_s$ and the thickness t, the conductivity σ is calculated, where $σ=1/(R_s t)$. The sheet resistance $R_s$ is measured by using an ST-2258C multifunctional digital four-probe tester (Suzhou Jingge Electronic Co., Ltd.), and the probe uses a linear probe head (2.0 mm). The test result is shown in the following table 1.

TABLE 1

| Weight percentages of CNTs in CNT dispersion liquids | Conductivity (S/m) |
| --- | --- |
| 1.9 wt % | 1 |
| 3.7 wt % | 5 |
| 5.55 wt % | 10 |
| 7.27 wt % | 12 |

From the result of table 1, if can be known that the conductivity of the composite membrane has increased to 10 S/m. As a comparison example, the conductivity of the MWCNT/chewing gum thin membrane prepared by arbitrarily mixing CNTs and a chewing gum is only 3 S/m. The data indicates that in the composite membrane of the present specific embodiment, aligned arrangement of CNTs helps obtain high conductivity.

Young's modulus calculation is performed on the composite membrane prepared by CNT dispersion liquids with different concentrations, and the result is shown in the following table 2 (each sample is tested for 7 times, and average values are taken).

TABLE 2

| Weight percentages of CNTs in CNT dispersion liquids | Young's modulus (Mpa) |
| --- | --- |
| 0 | 0.2 |
| 1.9 wt % | 0.5 |
| 3.7 wt % | 0.8 |
| 5.55 wt % | 1.3 |
| 7.27 wt % | 3.1 |

Figure 25:
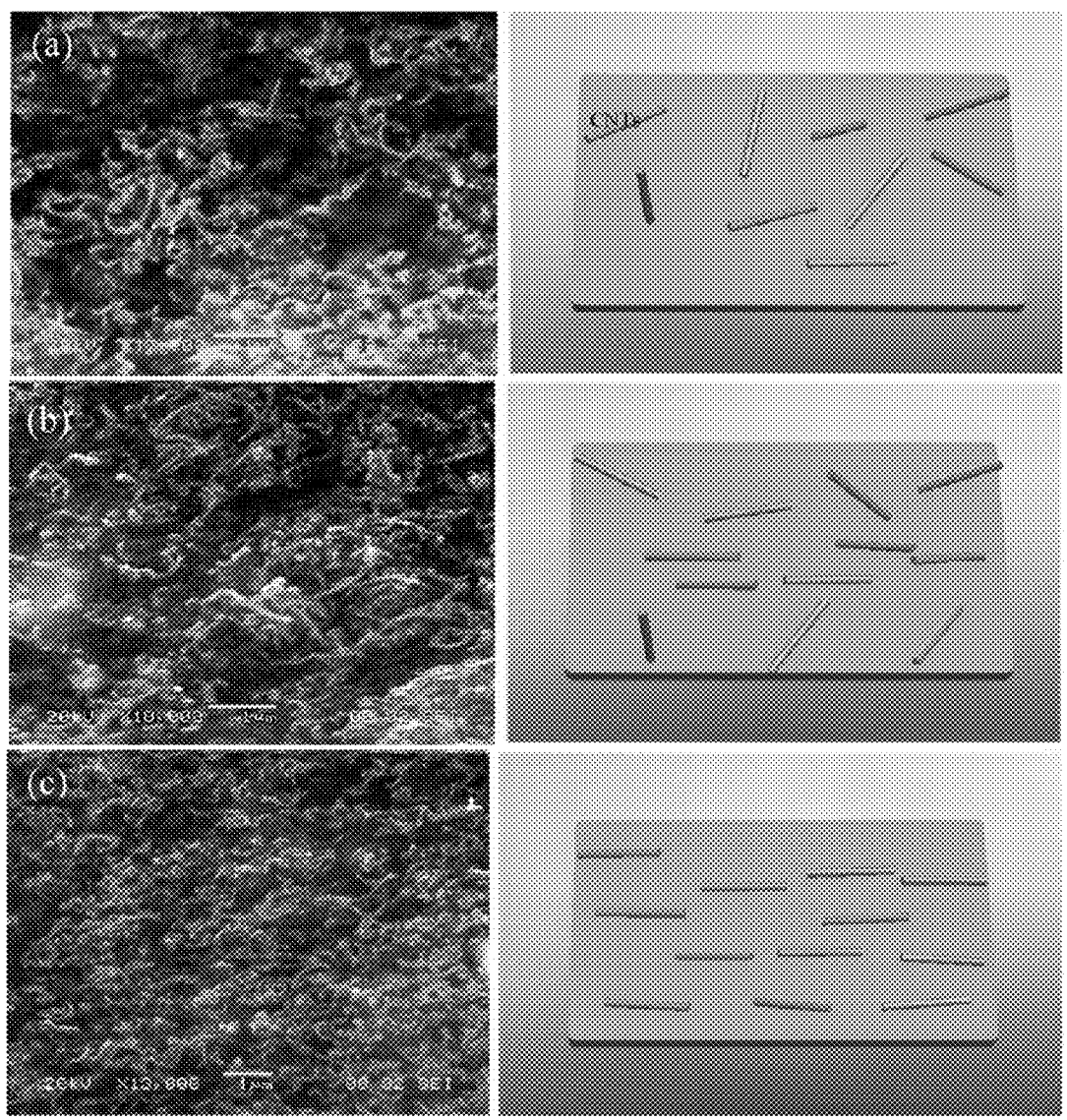
FIG. 25 is a schematic diagram of orientation of MWCNTs in a stretching and folding process of an embodiment of the present application.
Figure 26:
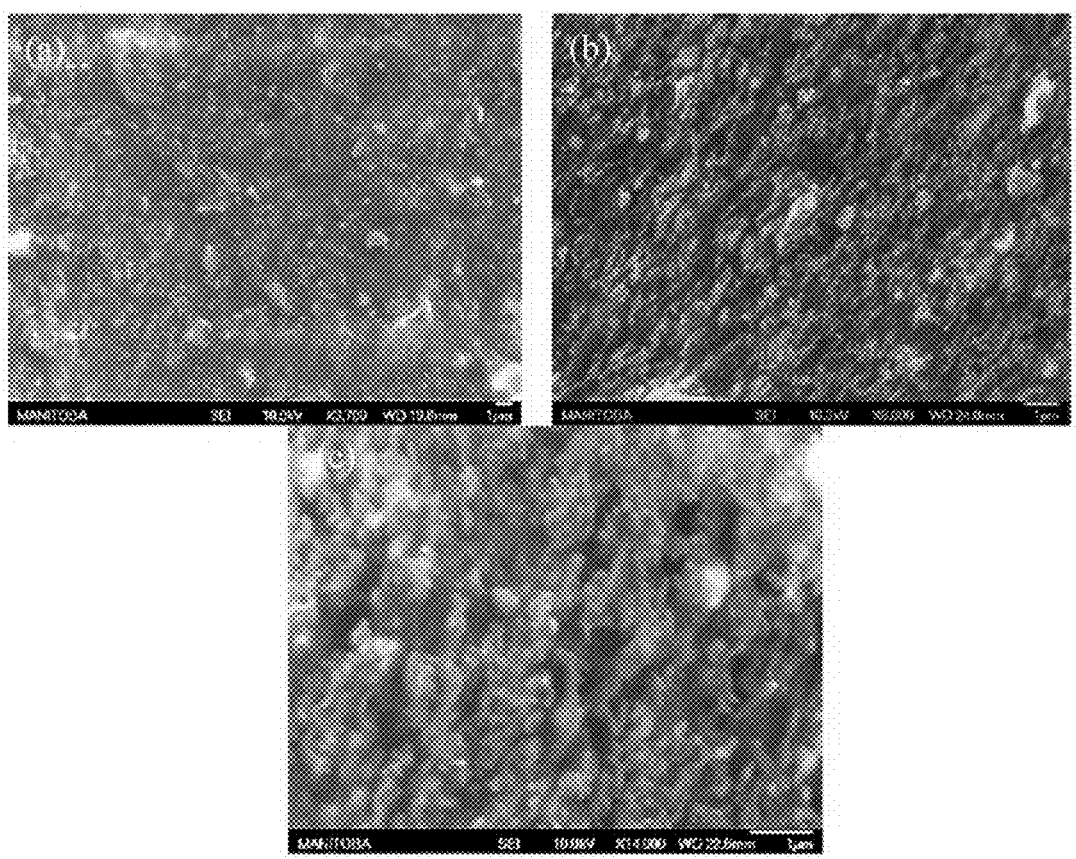
FIG. 26 is a schematic diagram of bundling of MWCNTs in a stretching and folding process of an embodiment of the present application.

7. Mechanism analysis:

The functional mechanism of the composite membrane in different working conditions is analyzed herein. The morphology of the composite membrane is observed by using two different SEM devices to comprehend first why the electrical resistance of the composite membrane is a function of CNT arrangement and second how this arrangement changes the resistance during a working process of the composite membrane. Upon analysis, two different mechanisms may exist. The first mechanism indicates the effect of aligned CNTs in increasing the conductivity (related to stretching and folding for multiple times), as shown in FIG. 25 and FIG. 26. The second mechanism indicates CNT orientation or deformation in a mechanical test process (FIG. 27).

FIG. 25 is a schematic diagram of orientation of MWCNTs during multiple stretching and folding processes. For the sample with no alignment of CNTs which is prepared without a stretching and folding process in FIG. 25a, there is less overlap of MWCNTs. After stretching and folding are performed on the chewing gum membrane for multiple times, there are more overlaps and connections of MWCNTs in a way that MWCNTs bundle tightly together (FIG. 25c and FIG. 26c), and therefore the tunneling resistance would not play a role until higher levels of strains are applied thereto. FIG. 25b illustrates the MWCNT arrangement in the composite membrane after stretching and folding for about 100 times. As shown in the drawings, it can be known that there are still some bundles of MWCNTs which are not oriented in the stretch direction. This can be because of the compressive stress (due to the Poisson effect). These bundles oriented perpendicularly to the axis of strain will be oriented by continuing the stretching and releasing process to make MWCNTs completed aligned, as shown in FIG. 25c.

As shown in FIG. 26, performing stretching and folding for multiple times causes nanotubes to buckle into waves. One possible reason is that after the thin membrane is stretched, relaxation to strain produces waves in the bundles that have been aligned by stretching. These aligned wavy bundles of MWCNTs cause more contact areas between CNTs and accordingly lead to an increase in the conductivity. These waves help the resistance response follow a linear trend in lower amplitudes (see FIG. 9 and FIG. 10), since MWCNTs are still in contact with each other. In this case, for high amplitudes, tunneling effects become prominent.

Figure 27:
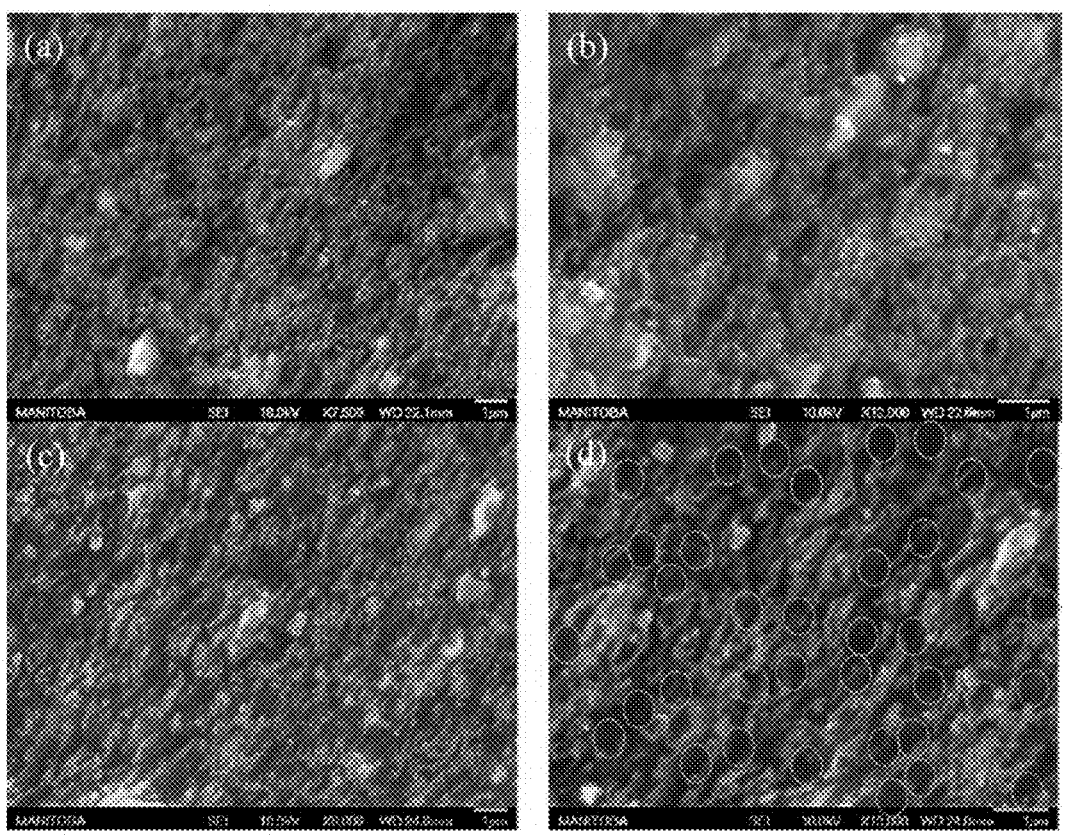
FIG. 27 is a schematic diagram of arrangement of MWCNTs of a composite membrane in a mechanical test process of an embodiment of the present application.

To evaluate a deformation behavior of the composite membrane under large stretching, mechanical tests are performed with SEM observation results shown in FIG. 27. Parts a and b of FIG. 27 illustrate arrangement of MWCNTs in the composite membrane before mechanical tests are performed, and parts c and d of FIG. 27 illustrate deformation of the composite membrane after 200% stretching. As shown in the drawings, before elongation, most of the MWCNT bundles are attached, but when the composite membrane is stretched 2 times the original size (FIG. 27c and FIG. 27d), some MWCNTs are disconnected. In the drawings, gaps between the MWCNT bundles are marked with circles for better comparison. This case promotes the tunneling effect and leads to nonlinear increase of the resistance (FIG. 9 and FIG. 10).

Electrical conduction mechanisms implemented when the composite membrane is exposed to water vapors are provided below, so as to analyze possible reasons of the humidity test result shown in FIG. 22 and FIG. 23. For the composite membrane with lower CNT concentrations (much lower than a percolation threshold), a distance between MWCNTs is large, and therefore ions in water can contribute in transferring electrons. Accordingly, with the increase of humidity, for lower CNT concentrations, the resistance decreases in a nonlinear trend, as shown in FIG. 22. On the other hand, when the CNT concentration increases, the CNT junction resistance controls the humidity sensing and electrons transferred between the CNTs rather than water ions; hence, the composite membrane becomes less sensitive to humidity changes in environments with higher CNT concentrations.

Based on the above, the present specific embodiment provides a facile method for preparing an elastic, attachable, low-cost, and conductive composite membrane. The composite membrane may be efficiently used for sensing muscle and joint motions of living bodies. Since the composite membrane can be patterned into various forms, it has wide applications in miniaturized sensors and biochips. According to tests, in terms of high sensitivity (G ranging from 12 to 25), high measurable strain (530% strain), high durability (1,000 stretch-release cycles, limited by the PDMS properties), facile fabrication, and cost efficiency, performances expressed by the composite membrane are superior to a measurement membrane used in any other strain sensor. Previous strain sensors cannot have characteristics of high strain detection and high sensitivity at the same time. For example, some strain sensors can monitor strains as high as 280%, but have a relatively low gauge factor, which is only in a range of 0.06 to 0.82. However, some strain sensors have the characteristic of high sensitivity, but lack good strain detection capability. The composite membrane of the present application has high sensitivity and high strain detection capability at the same time. In the present application, a moldable and plastic material, in particular, a chewing gum is innovatively applied to the field of biomedical applications for the first time, and an innovative facile method for aligning nanocarbon materials is provided; uniform and balanced dispersion is performed on the nanocarbon materials by means of multiple stretching and folding processes, so that good conductivity is implemented, and reaches 10 S/m. In addition, the prepared composite membrane may monitor humidity changes with high sensitivity, and may sense breathing, and may have good application prospects in the aspect of constructing a high-performance strain and humidity monitoring system.

The foregoing content is further detailed description made to the present application with reference to specific embodiments, and the present application cannot be determined to be limited only to the description. For persons of ordinary skill in the technical field to which the present application belongs, several replacements or obvious transformations that are made on a precondition of not departing from the idea of the present application and have same performance or use should be considered to fall into the protection scope of the present application.

What is claimed is:

1. A method for preparing a composite membrane, comprising the following steps: S1, preparing a nanocarbon material into a 0.5 to 20 wt % nanocarbon material dispersion liquid, wherein the nanocarbon material is a carbon nanotube or graphene; S2, preparing a moldable and plastic material; S3, wetting the plastic material by using the nanocarbon material dispersion liquid, stretching the plastic material along a first direction, and then folding the plastic material towards a second direction, wherein the second direction is opposite to the first direction, and repeating the stretching and folding process for 500 to 1,000 times; and S4, drying the plastic material processed in step S3 at a temperature ranging from 20 to 35° C., so as to prepare a composite membrane compounded by the plastic material and the nanocarbon material.

2. The method for preparing a composite membrane according to claim 1, wherein, in step S2, a chewed chewing gum is washed and air-dried as the plastic material; in step S3, the chewing gum is wetted by using the nanocarbon material dispersion liquid; the chewing gum is stretched along the first direction, and then is folded towards the second direction, wherein the second direction is opposite to the first direction; and the stretching and folding process is repeated for 500 to 1,000 times.

3. The method for preparing a composite membrane according to claim 2, wherein, in step S2, the chewing gum is positioned in a mixed solution prepared by ethanol and distilled water and is shaken for 10 to 14 h for washing, and then the chewing gum is air-dried at a temperature ranging from 20 to 35° C.

4. The method for preparing a composite membrane according to claim 1, wherein, the nanocarbon material is a carbon nanotube, and weight percentage of the carbon nanotube in the carbon nanotube dispersion liquid is 3.5 wt %-6 wt %.

5. The method for preparing a composite membrane according to claim 1, wherein step S1 is: adding a carbon nanotube solution to a surfactant water solution to obtain a mixed solution, and then performing sonication on the mixed solution to prepare the nanocarbon material dispersion liquid.

6. The method for preparing a composite membrane according to claim 5, wherein, in the sonication, the mixed solution is positioned in an ice-water environment, after 35 to 45 min of sonication, the mixed solution stays in the ice-water environment for 5 to 15 min, and then sonication is performed for 35 to 45 min.

7. The method for preparing a composite membrane according to claim 5, wherein, the surfactant is a block polyether macromolecular surfactant.

8. The method for preparing a composite membrane according to claim 1, wherein, in step S1, the carbon nanotube is one or more of a mixture of a singled-walled carbon nanotube and a multiwalled carbon nanotube.

9. A method for preparing a biosensor, comprising the following steps: P1, preparing a composite membrane according to the preparation method of claim 1; P2, positioning the composite membrane on a first thin membrane, and respectively attaching a first electrode wire and a second electrode wire to two ends of the composite membrane; and P3, covering a second thin membrane on a surface of the composite membrane, and drying at a temperature ranging from 20 to 35° C.

* * * * *

UNITED STATES PATENT AND TRADEMARK OFFICE
CERTIFICATE OF CORRECTION

PATENT NO. : 10,413,221 B2
APPLICATION NO. : 15/337900
DATED : September 17, 2019
INVENTOR(S) : Xing et al.

Page 1 of 1

It is certified that error appears in the above-identified patent and that said Letters Patent is hereby corrected as shown below:

On the Title Page

Item (72) Inventor is corrected to read:
--Malcolm Xing, Guangdong (CN);
Haitao Shang, Guangdong (CN);
Kun Jiang, Guangdong (CN)--.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*